(12) United States Patent
Miyazaki et al.

(10) Patent No.: US 10,379,081 B2
(45) Date of Patent: Aug. 13, 2019

(54) ANALYZER

(71) Applicant: Sumitomo Heavy Industries, Ltd., Tokyo (JP)

(72) Inventors: Shuji Miyazaki, Kanagawa (JP); Daiji Ichishima, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 941 days.

(21) Appl. No.: 14/524,626

(22) Filed: Oct. 27, 2014

(65) Prior Publication Data

US 2015/0127283 A1    May 7, 2015

(30) Foreign Application Priority Data

Nov. 1, 2013 (JP) ................... 2013-228374
Sep. 9, 2014 (JP) ................... 2014-183427

(51) Int. Cl.
 *G01N 27/72* (2006.01)
 *G01R 33/00* (2006.01)
 (Continued)

(52) U.S. Cl.
 CPC ......... *G01N 27/72* (2013.01); *G01N 15/1031* (2013.01); *G01R 33/0023* (2013.01); *G01R 33/12* (2013.01); *G06F 17/5009* (2013.01)

(58) Field of Classification Search
 CPC .... G01N 27/72; G01N 15/1031; G01R 33/12; G01R 33/0023; G06F 17/5009
 See application file for complete search history.

(56) References Cited

U.S. PATENT DOCUMENTS 8,280,699 B2    10/2012   Ichishima et al.
8,886,497 B1 *  11/2014   Vold .................. G06F 17/13
                                                   703/2

(Continued)

FOREIGN PATENT DOCUMENTS

JP    H11-146688 A     5/1999
JP    2009-037334 A    2/2009
JP    2012-128490 A    7/2012

OTHER PUBLICATIONS

Scherer, Stochastic Molecular Dynamics of Colloidal Particles, Jun. 2004, p. 442-447.*

(Continued)

*Primary Examiner* — Mohammad K Islam
(74) *Attorney, Agent, or Firm* — Michael Best & Friedrich LLP

(57) ABSTRACT

An analyzer includes a magnetic moment application unit configured to apply a magnetic moment to a particle system defined in a virtual space, a magnetic field calculation unit configured to calculate a magnetic physical quantity related to the particle system including particles, to which the magnetic moment is applied by the magnetic moment application unit, and a particle state calculation unit configured to numerically calculate a governing equation, which governs the movement of each particle, using the calculation result in the magnetic field calculation unit. The magnetic field calculation unit numerically calculates an induction magnetic field using induced magnetization induced in each particle due to a time variation in an external magnetic field and a magnetic field obtained by interaction between magnetic moments based on the induced magnetization.

7 Claims, 9 Drawing Sheets

(51) Int. Cl.
  *G01R 33/12*  (2006.01)
  *G01N 15/10*  (2006.01)
  *G06F 17/50*  (2006.01)

(56) References Cited

U.S. PATENT DOCUMENTS

| | | | | |
|---|---|---|---|---|
| 2002/0042698 | A1* | 4/2002 | Meuris | G06F 17/13 |
| | | | | 703/2 |
| 2002/0099510 | A1* | 7/2002 | Namiki | G01R 29/0892 |
| | | | | 702/66 |
| 2002/0104586 | A1* | 8/2002 | Morikawa | C21D 6/002 |
| | | | | 148/121 |
| 2007/0233405 | A1* | 10/2007 | Izumi | G01R 29/0871 |
| | | | | 702/57 |
| 2009/0278534 | A1* | 11/2009 | Kahlman | B82Y 25/00 |
| | | | | 324/252 |
| 2012/0101772 | A1* | 4/2012 | Frassati | G01D 5/142 |
| | | | | 702/150 |
| 2013/0123639 | A1* | 5/2013 | Ando | A61B 5/0059 |
| | | | | 600/473 |
| 2013/0166230 | A1* | 6/2013 | Shimizu | G01R 33/0064 |
| | | | | 702/57 |
| 2013/0231879 | A1 | 9/2013 | Ichishima et al. | |
| 2014/0357935 | A1* | 12/2014 | Ilmoniemi | A61N 2/006 |
| | | | | 600/13 |

OTHER PUBLICATIONS

Nakazawa, Comment on Geometric Interpretation of Ito Calculus on the Lattice, 2003, p. 1-8.*

Yoshika, The Quantum Hall Effect, Jan. 2002, p. 1-16.*

Scherer, Stochastic Molecular Dynamics of Colloidal Particles, p. 442-447 (Year: 2004).*

Nakazawa, Comment on Geometric Interpretation of Ito Calculus on the Lattice, p. 1-8 (Year: 2003).*

Yoshika, The Quantum Hall Effect, p. 1-16 (Year: 2002).*

Kyle J.M. Bishop et al.; "Nanoscale Forces and Their Uses in Self-Assembly," Small, vol. 5, No. 14, pp. 1600-1630, XP055172525, Jul. 17, 2009.

Extended Search Report issued in European Patent Application No. 14189983.1, dated Mar. 11, 2015.

* cited by examiner

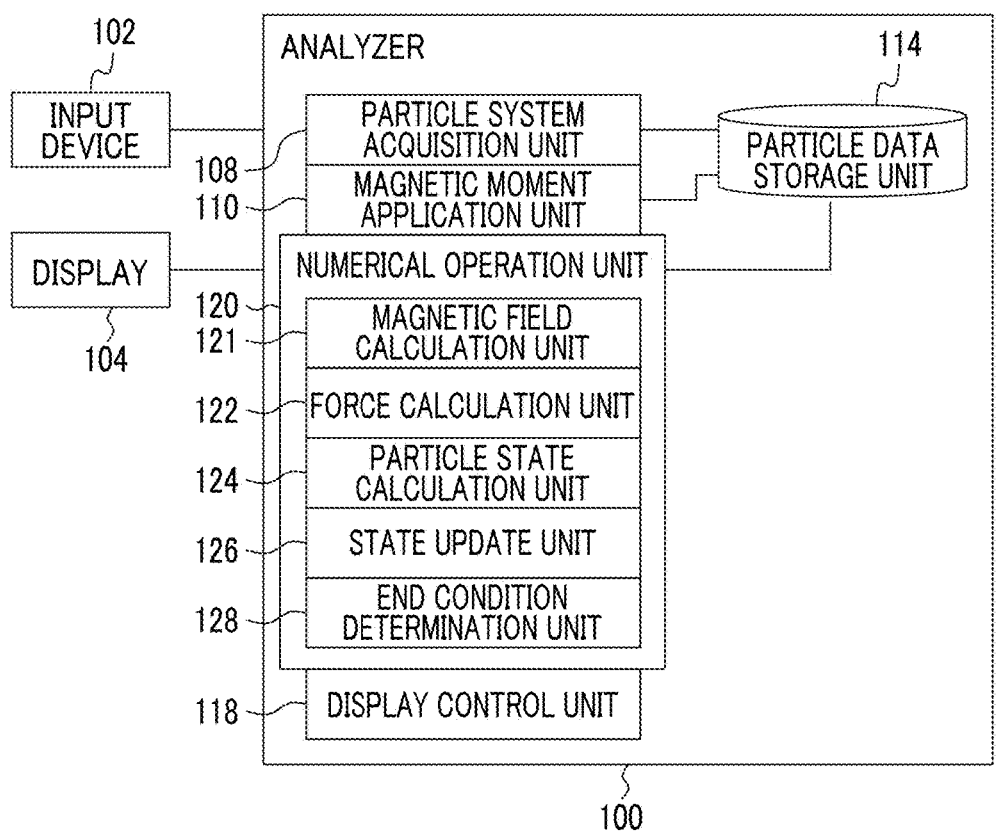

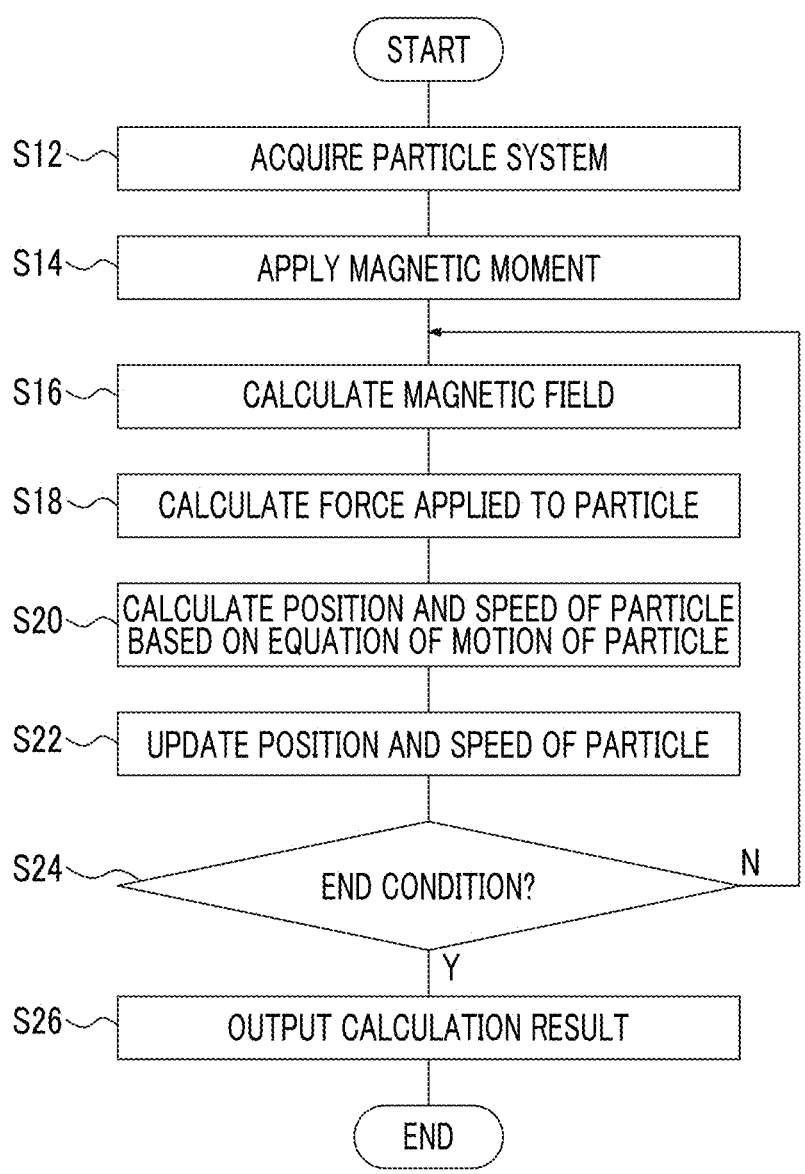

ANALYZER

RELATED APPLICATIONS

Priority is claimed to Japanese Patent Application No. 2013-228374, filed Nov. 1, 2013, the entire content of which is incorporated herein by reference.

BACKGROUND

Technical Field

The present invention relates to an analyzer which analyzes a particle system.

Description of Related Art

In recent years, with the improvement of computational capability of a computer, a simulation which incorporates magnetic field analysis is frequently used in the field of design and development of electric appliances, such as a motor. The use of the simulation can improve the speed of design and development since the simulation enables a certain degree of evaluation without actually producing a prototype.

For example, Japanese Unexamined Patent Application Publication No. 11-146688 describes a motor analyzer including an arithmetic processing unit which executes magnetic field analysis. The arithmetic processing unit executes torque calculation according to magnetostatic field analysis by a finite element method or according to a Maxwell stress method in response to external instructions based on user operations. Meshing is performed in the magnetostatic field analysis by the finite element method. The meshing is applied to a core region and a housing region, as well as an external air layer region. Other methods of magnetic field analysis include a difference method and a magnetic moment method.

SUMMARY

An analyzer according to an embodiment of the invention includes a magnetic moment application unit configured to apply a magnetic moment to a particle system defined in a virtual space, a magnetic field calculation unit configured to calculate a magnetic physical quantity related to the particle system including particles, to which the magnetic moment is applied by the magnetic moment application unit, and a particle state calculation unit configured to numerically calculate a governing equation, which governs the movement of each particle, using the calculation result in the magnetic field calculation unit. The magnetic field calculation unit numerically calculates an induction magnetic field using induced magnetization induced in each particle due to a time variation in an external magnetic field and a magnetic field obtained by interaction between magnetic moments based on the induced magnetization.

An analyzer according to another embodiment of the invention includes a magnetic moment application unit configured to apply a magnetic moment to a particle system defined in a virtual space, a magnetic field calculation unit configured to calculate a magnetic physical quantity related to the particle system including particles, to which the magnetic moment is applied by the magnetic moment application unit, and a particle state calculation unit configured to numerically calculate a governing equation, which governs the movement of each particle, using the calculation result in the magnetic field calculation unit. The magnetic field calculation unit numerically calculates an induction magnetic field in a particle group using an expression for an induction magnetic field derived by gauge transformation using a local gravity center vector representing the gravity center position of the particle group to be analyzed.

BRIEF DESCRIPTION OF THE DRAWINGS

FIG. 1 is a block diagram showing the function and configuration of an analyzer according to an embodiment.

FIG. 2 is a data structure diagram showing an example of a particle data holding unit of FIG. 1.

FIG. 3 is a flowchart showing an example of a sequence of processing in the analyzer of FIG. 1.

DETAILED DESCRIPTION

Figure 4:
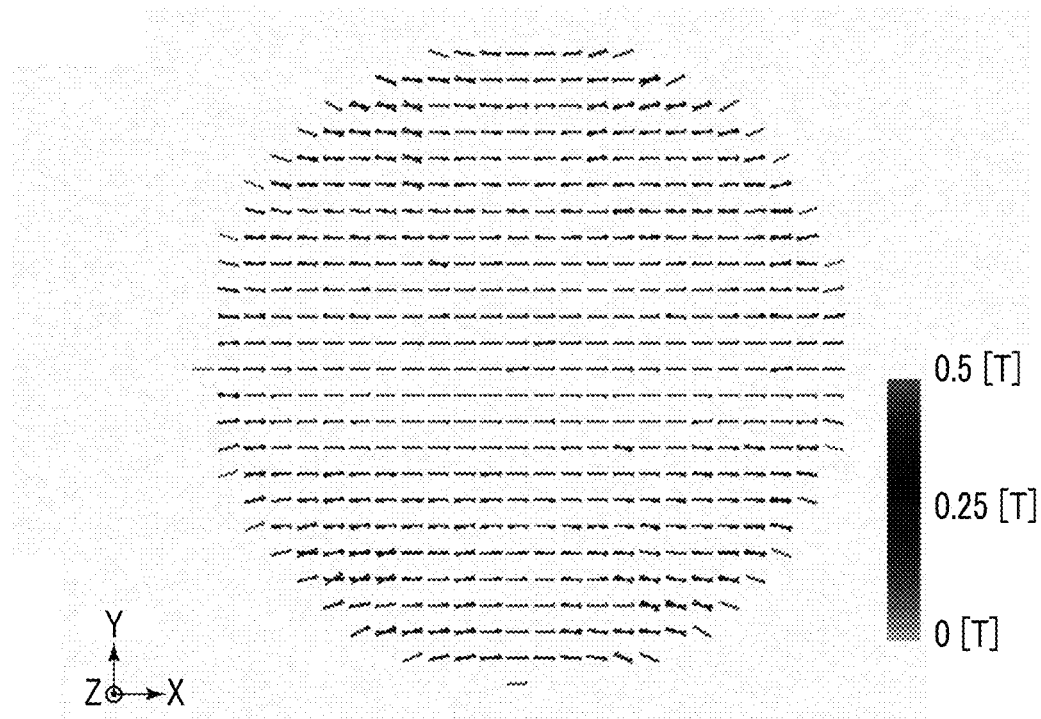
FIG. 4 is a diagram showing the calculation results corresponding to an expansion to $n=1$ order.

In the related art methods, the meshing is applied to an object to be analyzed. However, when the object to be analyzed is a fluid and if a fixed mesh is used with moving boundaries, the analysis is difficult. If the object to be analyzed is accompanied with large displacement of a magnetic body or a plastic body, the meshing is difficult. In particular, when the meshing is performed in magnetic field analysis including a rotor, such as a motor, polymerization of meshes (if the polymerization is single, this is the large displacement) makes the analysis difficult.

It is desirable to provide an analysis technique which enables preferred analysis of magnetic phenomenon in a simulation.

It is to be noted that any arbitrary combination of the above-described structural components or rearrangement of the structural components and the expressions of certain embodiments of the invention among a device, a method, a system, a computer program, a recording medium having a computer program recorded thereon, and the like are also effective as the embodiments of the invention.

Hereinafter, the same or similar structural components, members, and processing shown in the respective drawings are represented by the same reference numerals, and overlapping description will be appropriately omitted.

Embodiment

As methods of analyzing phenomenon of general material science using a computer based on classical mechanics or quantum mechanics, simulations based on a molecular dynamics method (hereinafter, referred to as "MD method"), a quantum molecular dynamics method, or a renormalized molecular dynamics (hereinafter, referred to as "RMD method") which is developed version of the MD method to operate with a macroscale system are known (for example, see Japanese Unexamined Patent Application Publication No. 2009-37334). To be precise, the MD method or the RMD method is a kinetic method (calculation of a physical quantity uses statistical mechanics), and the particle method is a method which discretizes a differential equation describing a continuum. However, in this specification, the MD method or the RMD method is referred to as the particle method.

Since the particle method can analyze not only static phenomenon but also dynamic phenomenon, such as flow, the particle method attracts attention as a simulation method replacing the above-described finite element method in which the object to be analyzed is primarily static phenomenon.

From a differential point of view, the particle method obtains a particle system to be analyzed by discretizing a continuum by particles. For example, when a fluid is analyzed in the particle method, it is often the case that the Navier-Stokes equation is discretized by particles.

From another or integral point of view, the particle method forms a continuum by collecting many particles. This is, for example, a view in which a large iron ball is formed by collecting and solidifying small iron particles.

In general, when calculating a magnetic field at a certain point in a space where many magnetic moments exist, due to superposition principle, the magnetic field at the certain point created by each magnetic moment is summed up over the magnetic moments. The inventors have found affinity between the method of calculating the magnetic field from a collection of magnetic moments and the particle method in the integral view, and have devised the application of a magnetic moment to each of particles in the particle method. With this, it is possible to broaden the cover range of the particle method to magnetic field analysis while maintaining the advantage of the particle method, the advantage that the particle method is effective for analysis of convection or large displacement.

The inventors have devised that it is possible to broaden the cover range of the particle method to dynamic magnetic field analysis including electromagnetic induction phenomenon by taking into consideration induced magnetization induced in each particle in addition to an interaction term between magnetic moments applied to the particles in the particle method. With this, it is possible to realize dynamic magnetic field analysis by the particle method for physical phenomenon, which is accompanied with large displacement and requires consideration concerning electromagnetic induction, such as interaction between a stator and a rotor in an induction motor.

FIG. 1 is a block diagram showing the functions and configuration of an analyzer 100 according to an embodiment. It should be understood that respective blocks shown in the drawing can be realized by hardware, for example, an element, such as a central processing unit (CPU) of a computer, or a mechanical device, or can be realized by software, for example, a computer program. In the drawing, functional blocks which are realized by cooperation of hardware and software are shown. Therefore, it should be understood by those skilled in the art in contact with this specification that these functional blocks can be realized by a combination of hardware and software in various ways.

In this embodiment, although a case where a particle system is analyzed based on the RMD method is described, it is obvious to those skilled in the art in contact with this specification that the technical concept of this embodiment can be applied to a case where the particle system is analyzed based other particle methods, such as an MD method without renormalization, a distinct element method (DEM), smoothed particle hydrodynamics (SPH), or moving particle semi-implicit (MPS).

The analyzer 100 is connected to an input device 102 and a display 104. The input device 102 may be a keyboard, a mouse, or the like which receives an input of a user related to processing executed on the analyzer 100. The input device 102 may be configured to receive an input from a network, such as Internet, or a recording medium, such as a CD or a DVD.

The analyzer 100 includes a particle system acquisition unit 108, a magnetic moment application unit 110, a numerical calculation unit 120, a display control unit 118, and a particle data storage unit 114.

The particle system acquisition unit 108 acquires data of a particle system having N (where N is a natural number) particles defined in a one, two, or three-dimensional virtual space based on input information acquired from the user through the input device 102. The particle system is a particle system which is renormalized using the RMD method.

The particle system acquisition unit 108 arranges the N particles in the virtual space based on the input information and applies a speed to each of the arranged particles. The particle system acquisition unit 108 registers a particle ID for specifying an arranged particle, the position of the particle, and the speed of the particle in the particle data storage unit 114 in association with one another.

The magnetic moment application unit 110 applies a magnetic moment to each of the particles of the particle system acquired by the particle system acquisition unit 108 based on the input information acquired from the user through the input device 102. For example, the magnetic moment application unit 110 requests the user to input the magnetic moment of each of the particles of the particle system through the display 104. The magnetic moment application unit 110 registers the input magnetic moment in the particle data storage unit 114 in association with the particle ID.

The following description will be provided assuming that all particles of the particle system are homogenous or equivalent and a potential energy function is based on pair potential and has the same form regardless of particles. However, it is obvious to those skilled in the art in contact with this specification that the technical concept of this embodiment can be applied to other cases.

The numerical calculation unit 120 numerically calculates a governing equation which governs the movement of each particle of the particle system represented by data stored in the particle data storage unit 114. In particular, the numerical calculation unit 120 performs repetitive calculation according to an equation of motion of a discretized particle. The equation of motion of the particle has a term dependent on the magnetic moment.

The numerical calculation unit 120 includes a magnetic field calculation unit 121, a force calculation unit 122, a particle state calculation unit 124, a state update unit 126, and an end condition determination unit 128.

The magnetic field calculation unit 121 calculates a magnetic field generated by the particle system represented by data stored in the particle data storage unit 114. The magnetic field calculation unit 121 calculates the magnetic field based on the magnetic moment of each particle stored in the particle data storage unit 114. The magnetic field is a magnetic physical quantity relating to the particle system. The magnetic field calculation unit 121 may calculate magnetic flux density or magnetization instead of or in addition to the magnetic field.

The force calculation unit 122 refers to data of the particle system stored in the particle data storage unit 114 and calculates a force applied to the particle based on the inter-particle distance for each particle of the particle system. The force applied to the particle includes a force based on interaction between the magnetic moments. The force calculation unit 122 determines particles (hereinafter, referred to as near particles) whose distance from an i-th (where $1 \leq i \leq N$) particle is less than a predetermined cut-off distance for the i-th particle of the particle system.

For each near particle, the force calculation unit 122 calculates a force applied to the i-th particle by the near particle based on the potential energy function between the near particle and the i-th particle and the distance between the near particle and the i-th particle. In particular, the force calculation unit 122 calculates the force from the value of the gradient of the potential energy function at the value of the distance between the near particle and the i-th particle. The force calculation unit 122 sums up the force applied to the i-th particle by the near particle for all near particles to calculate the force applied to the i-th particle.

The particle state calculation unit 124 refers to data of the particle system stored in the particle data storage unit 114 and applies the force calculated by the force calculation unit 122 to the equation of motion of the discretized particle for each particle of the particle system to calculate at least one of the position and speed of the particle. In this embodiment, the particle state calculation unit 124 calculates both the position and speed of the particle.

The particle state calculation unit 124 calculates the speed of the particle from the equation of motion of the discretized particle including the force calculated by the force calculation unit 122. The particle state calculation unit 124 substitutes the force calculated by the force calculation unit 122 in the equation of motion of the discretized particle using a predetermined minute time interval $\Delta t$ based on a predetermined numerical analysis method, such as a leapfrog method or a Euler method, for the i-th particle of the particle system, thereby calculating the speed of the particle. In the calculation, the speed of the particle calculated in the previous repetitive calculation cycle is used.

The particle state calculation unit 124 calculates the position of the particle based on the calculated speed of the particle. The particle state calculation unit 124 applies the calculated speed of the particle to a relationship expression of the position and speed of the discretized particle using the time interval $\Delta t$ based on a predetermined numerical analysis method for the i-th particle of the particle system, thereby calculating the position of the particle. In the calculation, the position of the particle calculated in the previous repetitive calculation cycle is used.

The state update unit 126 updates the position and speed of each particle of the particle system stored in the particle data storage unit 114 to the position and speed calculated by the particle state calculation unit 124.

The end condition determination unit 128 performs determination about whether or not to end repetitive calculation in the numerical calculation unit 120. An end condition for ending repetitive calculation is, for example, that repetitive calculation is performed a predetermined number times, an end instruction is received from the outside, or the particle system reaches a steady state. When the end condition is satisfied, the end condition determination unit 128 ends repetitive calculation in the numerical calculation unit 120. When the end condition is not satisfied, the end condition determination unit 128 returns the process to the force calculation unit 122. When this happens, the force calculation unit 122 calculates the force with the position and speed of the particle updated by the state update unit 126 again.

The display control unit 118 causes the display 104 to display the form of a time expansion of the particle system or the state of the particle system at a certain time based on the position, speed, and magnetic moment of each particle of the particle system represented by data stored in the particle data storage unit 114. The display may be performed in a form of a still image or a motion image.

FIG. 2 is a data structure diagram showing an example of the particle data storage unit 114. The particle data storage unit 114 stores the particle ID, the position of the particle, the speed of the particle, and the magnetic moment of the particle in association with one another.

In the above-described embodiment, an example of the storage unit is a hard disk or a memory. It should be understood by those skilled in the art in contact with this specification that the respective units can be realized by a CPU (not shown), a module of an installed application program, a module of a system program, a memory which temporarily stores the contents of data read from a hard disk, or the like based on the description of the specification.

The operation of the analyzer 100 having the above-described configuration will be described.

FIG. 3 is a flowchart showing a sequence of processing in the analyzer 100. The particle system acquisition unit 108 acquires a particle system which is renormalized based on the RMD method (S12). The magnetic moment application unit 110 applies a magnetic moment to each of particles of the acquired particle system (S14). The magnetic field calculation unit 121 calculates a magnetic field generated by the particle system (S16). The force calculation unit 122 calculates a force applied to a particle from the inter-particle distance and the magnetic moment of each particle (S18). The particle state calculation unit 124 calculates the speed and position of a particle from the equation of motion of the particle including the calculated force (S20). The state update unit 126 updates the position and speed of the particle stored in the particle data storage unit 114 to the calculated position and speed (S22). The end condition determination unit 128 performs determination about whether or not the end condition is satisfied (S24). When the end condition is not satisfied (N in S24), the process repeats Steps S16 to S22. When the end condition is satisfied (Y in S24), the display control unit 118 outputs the calculation result (S26).

In general, the particle method can perform preferred analysis of a dynamic object to be analyzed, such as a fluid, separation phenomenon, or cutting work.

Then, in the analyzer 100 of this embodiment, it is possible to realize the analysis based on the particle method and the magnetic field analysis based on the magnetic moment. Therefore, it is possible to analyze a dynamic object to be analyzed with high accuracy and in a short time, including a magnetic property, such as a magnetic field.

For example, when the object to be analyzed is iron sand, it is difficult to simulate the object since preferred arrangement of mesh is not possible with a related art mesh-based analysis method, such as the finite element method. Therefore, in the analyzer 100 of this embodiment, it is possible to perform preferred analysis of iron sand with the particle method in consideration of the magnetic property of iron sand.

For example, if the object to be analyzed is a motor, the related art mesh-based analysis method is not effective to the object since a rotor rotates with respect to a stator, and allows static analysis only. However, in the analyzer 100 of this embodiment, it is possible to dynamically analyze magnetic interaction between the rotor and the stator while simulating the rotation of the rotor using the particle method with high accuracy. Furthermore, even if the object to be analyzed includes electromagnetic induction phenomenon, such as an induction motor, induced magnetization in consideration of electromagnetic induction phenomenon and a magnetic moment based on the induced magnetization are applied, whereby it is possible to analyze magnetic interaction with a time variation in a magnetic field.

Hereinafter, the principle of the analysis method used for the analyzer 100 will be described.

The magnetic field can be obtained from a macroscopic vector potential

[Equation 1]

$$A(x) = \frac{\mu_0}{4\pi} \int \frac{J(x')}{|x-x'|} d^3 x'$$

as follows. The direction of spin is defined as a z axis, and a is defined as a radius of an atom. A circle current which generates spin $S_{jz}$ (magnetic moment $m_{jz}$) is expressed as follows.

[Equation 2]

$$I_j = \frac{m_{jz}}{\pi a^2}, \quad m_{jz} = g\mu_B S_{jz}$$

A magnetic field generated by a single spin at a lattice point j is expressed as follows.

[Equation 3]

$$B_r(x_p - x_j) = \frac{\mu_0 m_{jz}}{2\pi a r_{pj}} \sum_{n=0}^{\infty} \frac{(-1)^n (2n+1)!!}{2^n n!} \frac{r_{pj<}^{2n+1}}{r_{pj>}^{2n+2}} P_{2n+1}(\cos\theta_j) \quad (P\cdot 1)$$

$$B_\theta(x_p - x_j) = \qquad (P\cdot 2)$$

$$-\frac{\mu_0 m_{jz}}{4\pi} \sum_{n=0}^{\infty} \frac{(-1)^n (2n+1)!!}{2^n (n+1)!} \left\{ \begin{array}{c} -\left(\frac{2n+2}{2n+1}\right)\frac{1}{a^3}\left(\frac{r_{pj}}{a}\right)^{2n} \\ \frac{1}{r_{pj}^3}\left(\frac{a}{r_{pj}}\right)^{2n} \end{array} \right\} P_{2n+1}^1(\cos\theta_j)$$

$$B_\phi(x_p - x_j) = 0 \qquad (P\cdot 3)$$

Here, the following relationship is established.

[Equation 4]

$$r_{pj} = |x_p - x_j|, \quad \cos\theta_j = \frac{z_p - z_j}{r_{pj}}$$

If only n=0 is left, the magnetic field becomes equivalent to the magnetic field created by a sphere which is uniformly magnetized.

[Equation 5]

$$M_j = m_j \bigg/ \frac{4}{3}\pi a^3$$

When this method is applied to a bulk spherical body, if only n=0 is used, uniform magnetization may not be obtained, and the result will be similar to the magnetic moment method. This may be improved by adding higher-order terms. Uniform magnetization is obtained in the FEM.

The transformation to a Cartesian coordinate system (using the following expression) is performed.

$$x_{pj} = r_{pj} \sin\theta_j \cos\phi_j, y_{pj} = r_{pj} \sin\theta_j \sin\phi_j \qquad [\text{Equation 6}]$$

Then, the following expressions are defined.

[Equation 7]

$$B_x(x_p - x_j; m_{jz}) = (B_r(m_z)\sin\theta_j + B_\theta(m_z)\cos\theta_j)\cos\phi_j \qquad (P\cdot 4)$$

$$= (B_r + B_\theta \cos\theta_j)\frac{x_{pj}}{r_{pj}}$$

$$B_y(x_p - x_j; m_{jz}) = (B_r(m_z)\sin\theta_j + B_\theta(m_z)\cos\theta_j)\sin\phi_j \qquad (P\cdot 5)$$

$$= (B_r + B_\theta \cos\theta_j)\frac{y_{pj}}{r_{pj}}$$

$$B_z(x_p - x_j; m_{jz}) = B_r(m_z)\cos\theta_j - B_\theta(m_z)\sin\theta_j \qquad (P\cdot 6)$$

Here, it should be noted that, when $\sin\theta_j=0$, $B_x=B_y=0$ from $B_\theta=0$. The magnetic fields when the magnetic moments $m_x$ and $m_y$ are respectively parallel to the x axis and the y axis are obtained in a similar way.

[Equation 8]

$$B(; m_x), B(; m_y)$$

[Equation 9]

$$B_y(x_p - x_j; m_{jx}) = (B_r(m_x)\sin\theta_j + B_\theta(m_x)\cos\theta_j)\cos\phi_j \qquad (P\cdot 7)$$

$$= (B_r + B_\theta \cos\theta_j)\frac{y_{pj}}{r_{pj}}$$

$$B_z(x_p - x_j; m_{jx}) = (B_r(m_x)\sin\theta_j + B_\theta(m_x)\cos\theta_j)\sin\phi_j \qquad (P\cdot 8)$$

$$= (B_r + B_\theta \cos\theta_j)\frac{z_{pj}}{r_{pj}}$$

$$B_x(x_p - x_j; m_{jx}) = B_r(m_x)\cos\theta_j - B_\theta(m_x)\sin\theta_j \qquad (P\cdot 9)$$

$$B_z(x_p - x_j; m_{jy}) = (B_r(m_y)\sin\theta_j + B_\theta(m_y)\cos\theta_j)\cos\phi_j \qquad (P\cdot 10)$$

$$= (B_r + B_\theta \cos\theta_j)\frac{z_{pj}}{r_{pj}}$$

$$B_x(x_p - x_j; m_{jy}) = (B_r(m_y)\sin\theta_j + B_\theta(m_y)\cos\theta_j)\sin\phi_j \qquad (P\cdot 11)$$

$$= (B_r + B_\theta \cos\theta_j)\frac{x_{pj}}{r_{pj}}$$

$$B_y(x_p - x_j; m_{jy}) = B_r(m_y)\cos\theta_j - B_\theta(m_y)\sin\theta_j \qquad (P\cdot 12)$$

The magnetic field $$B_m \quad \text{[Equation 11]}$$

at $$x_p \quad \text{[Equation 10]}$$

(contributions to N spins) is as follows.

[Equation 12]

$$B_m(x_p) = \sum_{j \neq p}^{N} [B(x_p - x_j; m_{jx}) + B(x_p - x_j; m_{jy}) + B(x_p - x_j; m_{jz})] \quad (P.13)$$

$$M_p = \frac{3}{\mu_0}\left(\frac{\mu - \mu_0}{\mu + 2\mu_0}\right) B_o(x_p) \quad (P.14)$$

$$B_o(x_p) = B_m(x_p) + \mu_0 H_{ext} \quad (P.15)$$

$$m_p = (m_{jx}, m_{jy}, m_{jz}) = \frac{4}{3}\pi a^3 M_p \quad (P.16)$$

Here, the following expression means the total external field.

$$B_o \quad \text{[Equation 13]}$$

By combining P-14 and P-15, the magnetic moment $m_p$ is obtained. The magnetic field generated outside the magnetic body is expressed by P-15, and the magnetic field generated inside the magnetic body is expressed by the following expression.

[Equation 14]

$$B_{in} = B_o + \frac{2\mu_o}{3} M \quad (P\cdot 17)$$

$$H_{in} = \frac{1}{\mu_o} B_o - \frac{1}{3} M \quad (P\cdot 18)$$

P-14 satisfies the following expression in consideration of a demagnetizing field due to magnetization generated on the surface of the sphere.

$$\nabla \cdot M_p = 0 \quad \text{[Equation 15]}$$

P-13 is slow to converge since the matrix is not a superdiagonal angle (j=p is excluded). Thus, a solution is obtained from the following equation of motion.

[Equation 16]

$$\mathcal{L} = \sum_i \left[\frac{1}{2} m_v (1 + \chi)(\dot{m}_i \cdot \dot{m}_i) - \frac{1}{2}(m_i - \alpha B_o(r_i))^2\right] \quad (P\cdot 19)$$

$$m_v \frac{d\dot{m}_i}{dt} = -\frac{1}{1+\chi}(m_i - \alpha B_o(r_i)) - \gamma \dot{m}_i \quad (P\cdot 20)$$

$$\alpha = \frac{4\pi a^3}{\mu_o}\left(\frac{\mu - \mu_o}{\mu + 2\mu_o}\right) \quad (P\cdot 21)$$

Here, $m_v = 5 \times 10^{-2} dt^2$ is a virtual mass and $\gamma = m_v/(10\ dt)$ is a damping coefficient.

It is possible to realize further acceleration with an addition of FIRE (see Erik Bitzek et al., "Structural Relaxation Made Simple", Physical Review Letters, Oct. 27, 2006, 97). The code of the FIRE is shown below. The calculation result is 10.05 [s] under the condition that the number of particles is 802 and the residual is $<10^{-8}$. The residual is not below $10^{-5}$ without the FIRE.

Ordinary Step
Calculate m, force, and $\dot{m}$ from Eq.(P•20)
Fire Step

P=force·$\dot{m}$;

$\dot{m}_a=|\dot{m}|, f_a=|force|=DBL\_MIN$;

$\dot{m}=\dot{m}(1.0-\alpha)+(force/f_a)\dot{m}_a\alpha;$ [Equation 17]

if (P>0.0) n++;
if (n>5){α=0.99α; n=0;}
if (P<=0.0){m=0.0; a=0.1; n=0;}

Special cases of the Legendre functions and the associated Legendre function are listed below (x: =cos $\theta_j$)

[Equation 18]

$$P_0(x) = 1 \quad (P.22)$$

$$P_1(x) = x \quad (P.23)$$

$$P_2(x) = \frac{1}{2}(3x^2 - 1) \quad (P.24)$$

$$P_3(x) = \frac{1}{2}(5x^2 - 3x) \quad (P.25)$$

$$P_4(x) = \frac{1}{8}(35x^4 - 30x^2 + 3) \quad (P.26)$$

$$P_5(x) = \frac{1}{8}(63x^5 - 70x^3 + 15x) \quad (P.27)$$

and $\quad (P.28)$ $$P_1^1(x) = -(1 - x^2)^{1/2} \quad (P.29)$$

$$P_3^1(x) = -\frac{3}{2}(1 - x^2)^{1/2}(5x^2 - 1) \quad (P.30)$$

$$P_3^2(x) = 15(1 - x^2)x \quad (P.31)$$

$$P_3^3(x) = -15(1 - x^2)^{3/2} \quad (P.32)$$

$$P_5^1(x) = -\frac{1}{8}(1 - x^2)^{1/2}(315x^4 - 210x^2 + 15) \quad (P.33)$$

Hereinafter, the magnetization $$M \quad \text{[Equation 19]}$$

of a magnetic sphere (the magnetic susceptibility is 999) in a uniform external field of $B_{ox}=0.1$ [T] in the x-axis direction is calculated, and the result of the calculation is shown below.

The number of particles (atoms) forming the sphere is 4009 and the particles are arranged in an fcc structure. The exact solution is expressed as follows.

$$M = \frac{3}{\mu_o}\left(\frac{\mu - \mu_o}{\mu + 2\mu_o}\right) B_o \quad \text{[Equation 20]}$$

FIGS. 4, 5, 6, and 7 show the results of the first to fourth orders of multipole expansion. Cross-sections which pass the center are shown. If the order of the multipole expansion increases, it can be seen that the results get closer to the exact solution. If the order is low, the convergence is deteriorated. Most of the calculation time is occupied with calls for spherical harmonics.

FIG. 4 is a diagram showing the calculation results corresponding to an expansion to n=1 order. The calculation value is 0.346231 [T] on average with respect to the exact solution $\mu_o M_x$=0.2991 [T]. It can be seen that the magnetization is uniform and parallel to the external field $B_x$=0.1 [T]. The residual is equal to or less than 1e-13 and the calculation time is about 80 minutes.

Figure 5:
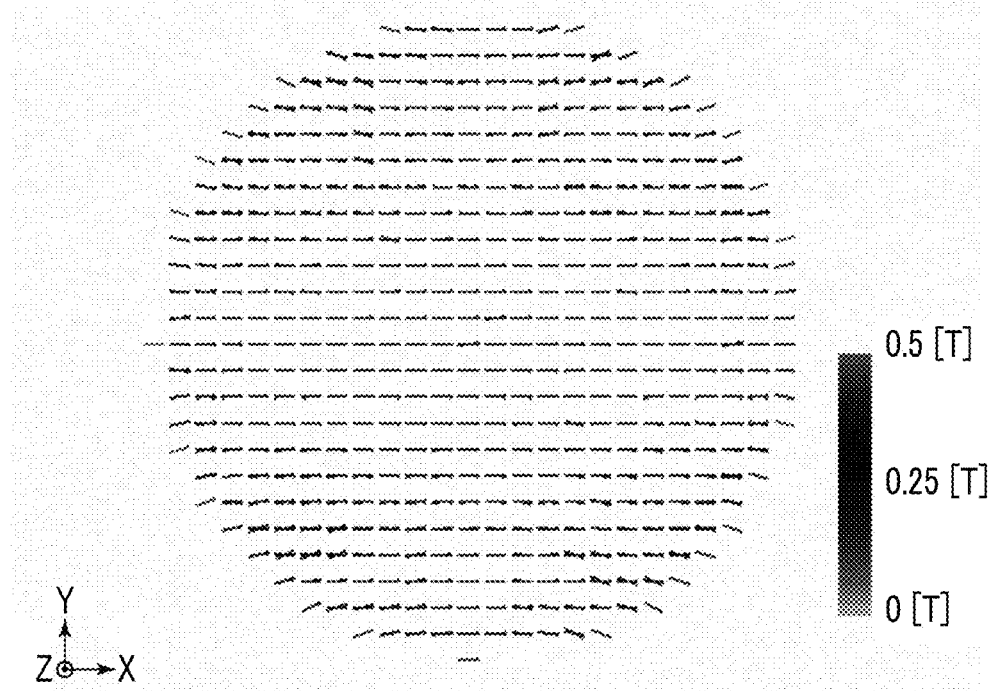
FIG. 5 is a diagram showing the calculation results corresponding to an expansion to $n=2$ order.

FIG. 5 is a diagram showing the calculation results corresponding to an expansion to n=2 order. The calculation value is 0.321891 [T] on average with respect to the exact solution $\mu_o M_x$=0.2991 [T]. It can be seen that the magnetization is uniform and parallel to the external field $B_x$=0.1 [T]. The residual is equal to or less than 1e-8 and the calculation time is about 3 hours. The residual does not fall below 1e-9.

Figure 6:
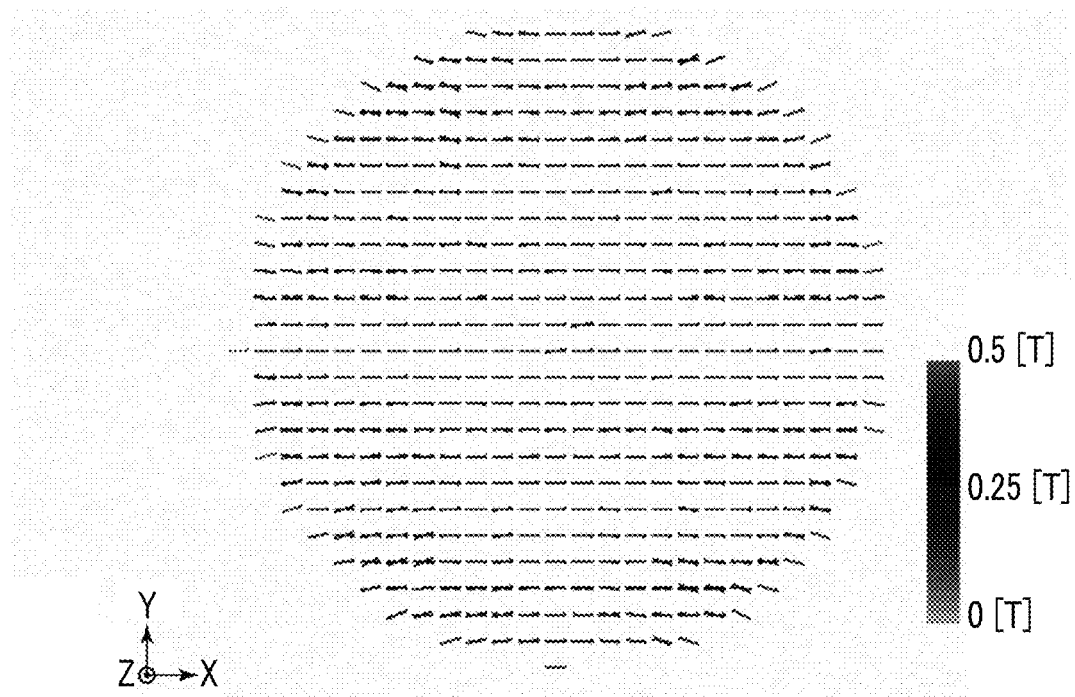
FIG. 6 is a diagram showing the calculation results corresponding to an expansion to $n=3$ order.

FIG. 6 is a diagram showing calculation results corresponding to an expansion to n=3 order. The calculation value is 0.312444 [T] on average with respect to the exact solution $\mu_o M_x$=0.2991 [T]. It can be seen that the magnetization is uniform and parallel to the external field $B_x$=0.1 [T].

Figure 7:
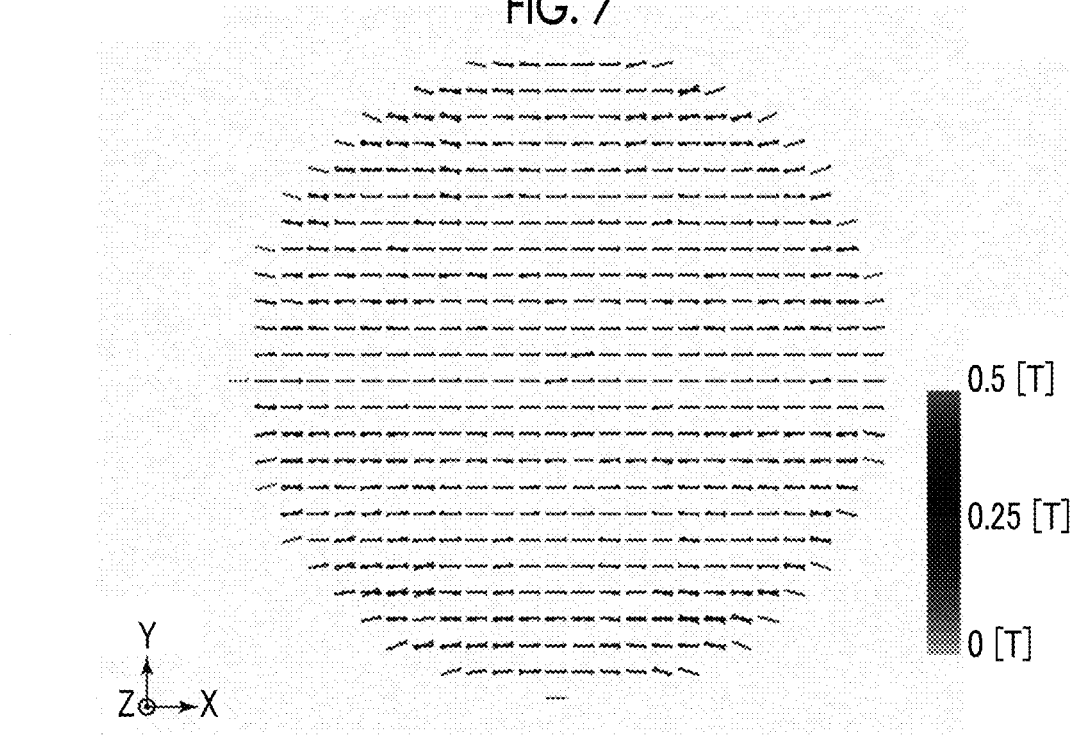
FIG. 7 is a diagram showing the calculation results corresponding to an expansion to $n=4$ order.

FIG. 7 is a diagram showing calculation results corresponding to an expansion to n=4 order. The calculation value is 0.312222 [T] on average with respect to the exact solution $\mu_o M_x$=0.2991 [T]. It can be seen that the magnetization is uniform and parallel to the external field $B_x$=0.1 [T]. The residual does not fall below 1e-9 after about 5 hours.

Figure 8:
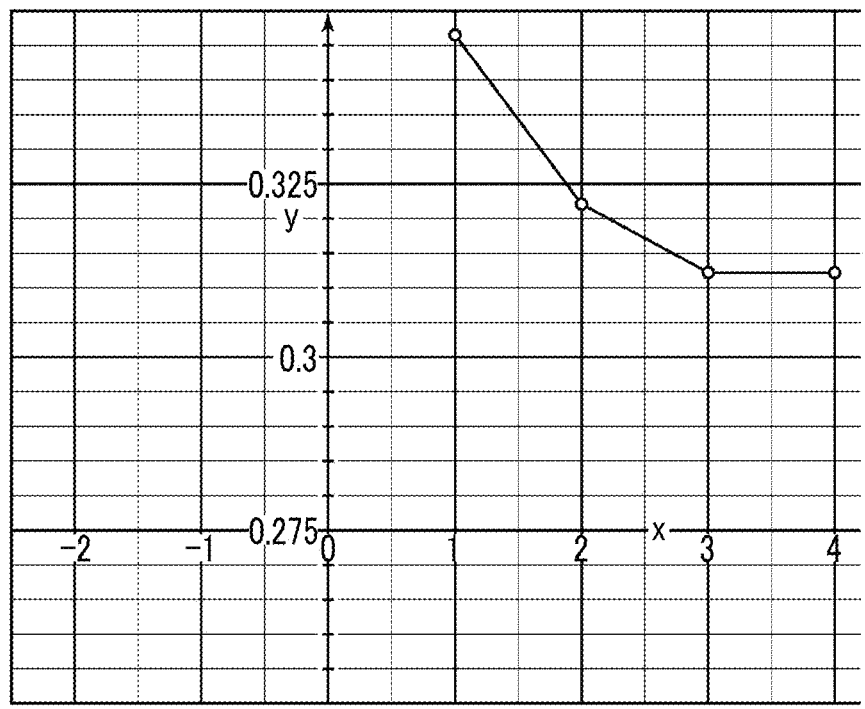
FIG. 8 is a diagram showing the relationship between the orders of spherical harmonics and calculation values.

FIG. 8 is a diagram showing the relationship between the orders of spherical harmonics and calculation values. It can be seen that a higher order gives results closer to the exact solution.

The principle of the analysis method used for the analyzer 100 may be described as follows.

[Equation 21]

$$\mathcal{L} = \mathcal{L}_{MD} + \mathcal{L}_{ED} + \mathcal{L}_{EM} \quad (Q\text{-}1)$$

$$\mathcal{L}_{MD} = \sum_p^N \left[ \frac{1}{2} M_p V_p^2 - \Phi(x_p) - eA(x_p) \cdot V_p \right] \quad (Q\text{-}2)$$

$$\mathcal{L}_{ED} = \sum_e^N \left[ \frac{1}{2} m_e v_e^2 + eA(x_e) \cdot v_e \right] \quad (Q\text{-}3)$$

$$\mathcal{L}_{EM} = \sum_m^N \delta V_m \left[ \frac{\mu_0}{2} m_v (\dot{H}_{om} \cdot \dot{H}_{om}) - \frac{\mu_0}{2} \lambda (H_{om} - H_o(x_m))^2 \right] \quad (Q\text{-}4)$$

$M_p$ is a mass of a nucleus, and $m_e$ is a mass of an electron. e is (an absolute value of) a charge of a nucleus or an electron. The charge and the mass of an electron may not explicitly appear since the charge is converted to a current and the mass of an electron is added to the mass of a nucleus to give a mass M of an atom in the end. $\delta V$ is a volume of the magnetic sphere, $m_v$ is a virtual mass, and $\lambda_i$ is a Lagrangian undetermined coefficient. To satisfy constraints rigorously, it is necessary to use convergence calculation like the SHAKE method; however, in this method, it is assumed that $\lambda_i$=1 and small vibrations around the true solution are treated as errors.

The direction of spin is defined as a z axis, and a is a radius of an atom. A circle current which generates spin $S_{jz}$ (magnetic moment $m_{jz}$) at a lattice point j is expressed as follows.

$$I_j = \frac{m_{jz}}{\pi a^2}, \; m_{jz} = g \mu_B S_{jz} \quad [\text{Equation 22}]$$

Therefore, the magnetic field can be obtained from the macroscopic vector potential $$A(x) = \frac{\mu_0}{4\pi} \int \frac{J(x')}{|x - x'|} d^3 x' \quad [\text{Equation 23}]$$

as follows.

[Equation 24]

$$H_r(r_{pj}) = \frac{m_{jz}}{2\pi a r_{pj}} \sum_{n=0}^{\infty} \frac{(-1)^n (2n+1)!!}{2^n n!} \frac{r_{pj<}^{2n+1}}{r_{pj>}^{2n+2}} P_{2n+1}(\cos\theta_j) \quad (Q.5)$$

$$H_\theta(r_{pj}) = \quad (Q.6)$$

$$-\frac{m_{jz}}{4\pi} \sum_{n=0}^{\infty} \frac{(-1)^n (2n+1)!!}{2^n (n+1)!} \left\{ \begin{array}{c} -\left(\frac{2n+2}{2n+1}\right)\frac{1}{a^3}\left(\frac{r_{pj}}{a}\right)^{2n} \\ \frac{1}{r_{pj}^3}\left(\frac{a}{r_{pj}}\right)^{2n} \end{array} \right\} P_{2n+1}^1(\cos\theta_j)$$

$$H_\phi(r_{pj}) = 0 \quad (Q.7)$$

Here, the following relationship is established.

$$r_{pj} = |x_p - x_j|, \; \cos\theta_j = \frac{z_p - z_j}{r_{pj}} \quad [\text{Equation 25}]$$

If only n=0 is left, the magnetic field becomes equivalent to the magnetic field created by a sphere which is uniformly magnetized.

$$M_j = m_j \Big/ \frac{4}{3}\pi a^3 \quad [\text{Equation 26}]$$

The transformation to a Cartesian coordinate system (using the following expression) is performed.

$$x_{pj} = r_{pj} \sin\theta_j \cos\phi_j, y_{pj} = r_{pj} \sin\theta_j \sin\phi_j \quad [\text{Equation 27}]$$

Then, the following expressions are defined.

[Equation 28]

$$H_x(r_{pj}; m_{jz}) = \{H_r(r_{pj}; m_z)\sin\theta_j + H_\theta(r_{pj}; m_z)\cos\theta_j\}\cos\phi_j \quad (Q.8)$$
$$= (H_r + H_\theta \cot\theta_j)\frac{x_{pj}}{r_{pj}}$$

$$H_y(r_{pj}; m_{jz}) = \{H_r(r_{pj}; m_z)\sin\theta_j + H_\theta(r_{pj}; m_z)\cos\theta_j\}\sin\phi_j \quad (Q.9)$$
$$= (H_r + H_\theta \cot\theta_j)\frac{y_{pj}}{r_{pj}}$$

$$H_z(r_{pj}; m_{jz}) = H_r(r_{pj}; m_z)\cos\theta_j - H_\theta(r_{pj}; m_z)\sin\theta_j \quad (Q.10)$$

Here, it should be noted that, when $\sin\theta_j$=0, $H_x$=$H_y$=0 from $H_\theta$=0. The magnetic fields $$H(;m_x), H(;m_y) \quad [\text{Equation 29}]$$

when the magnetic moments $m_x$ and $m_y$ are respectively parallel to the x axis and the y axis are obtained in a similar way.

[Equation 30]

$$H_y(r_{pj}; m_{jx}) = \{H_r(r_{pj}; m_x)\sin\theta_j + H_\theta(r_{pj}; m_x)\cos\theta_j\}\cos\phi_j \quad (Q.11)$$
$$= (H_r + H_\theta \cot\theta_j)\frac{y_{pj}}{r_{pj}}$$

$$H_z(r_{pj}; m_{jx}) = \{H_r(r_{pj}; m_x)\sin\theta_j + H_\theta(r_{pj}; m_x)\cos\theta_j\}\sin\phi_j \quad (Q.12)$$
$$= (H_r + H_\theta \cot\theta_j)\frac{z_{pj}}{r_{pj}}$$

$$H_x(r_{pj}; m_{jx}) = H_r(r_{pj}; m_x)\cos\theta_j - H_\theta(r_{pj}; m_x)\sin\theta_j \quad (Q.13)$$

$$\cos\theta_j = \frac{x_p - x_j}{r_{pj}} \quad (Q.14)$$

$$H_z(r_{pj}; m_{jy}) = \{H_r(r_{pj}; m_y)\sin\theta_j + H_\theta(r_{pj}; m_y)\cos\theta_j\}\cos\phi_j \quad (Q.15)$$
$$= (H_r + H_\theta \cot\theta_j)\frac{z_{pj}}{r_{pj}}$$

$$H_x(r_{pj}; m_{jy}) = \{H_r(r_{pj}; m_y)\sin\theta_j + H_\theta(r_{pj}; m_y)\cos\theta_j\}\sin\phi_j \quad (Q.16)$$
$$= (H_r + H_\theta \cot\theta_j)\frac{x_{pj}}{r_{pj}}$$

$$H_y(r_{pj}; m_{jy}) = H_r(r_{pj}; m_y)\cos\theta_j - H_\theta(r_{pj}; m_y)\sin\theta_j \quad (Q.17)$$

$$\cos\theta_j = \frac{y_p - y_j}{r_{pj}} \quad (Q.18)$$

The external magnetic field (contributions from N spins)

$$H_m \quad \text{[Equation 32]}$$

felt by a moment at $$x_p \quad \text{[Equation 31]}$$

is expressed as follows.

[Equation 33]

$$H_m(x_p) = \sum_{j \neq p}^{N} [H(r_{pj}; m_{jx}) + H(r_{pj}; m_{jy}) + H(r_{pj}; m_{jz})] \quad (Q.19)$$

$$m_p = (m_{px}, m_{py}, m_{pz}) = M_p \delta V_p \quad (Q.20)$$

The Induction Magnetic Field $$H_{ind} \quad \text{[Equation 34]}$$

is derived from the following expression when a p point is inside a conductor

[Equation 35]

$$H_{ind}^{(i)}(x_p) = M_{ant}(x_p) + \frac{1}{4\pi}\sum_j \frac{3n(n \cdot m_{ant}^j) - m_{ant}^j}{x_{pj}^3} \quad (Q.21)$$

$$M_{ant}(x_p) = -C_1 \sum_j \sigma_j G(x_{pj})\frac{\mathcal{D}B_j}{\mathcal{D}t} \quad (Q.21\text{-}2)$$

$$G(x_{pj}) = \begin{cases} \frac{1}{3}\frac{a_j^3}{x_{pj}} & x_{pj} > a_j \\ \frac{a_j^2}{2} - \frac{x_{pj}^2}{6} & x_{pj} < a_j \end{cases} \quad (Q.21\text{-}3)$$

$$m_{ant}^j = C_2 M_{ant}(x_j)\delta V_j \quad (Q.21\text{-}4)$$

and is derived from the following expression when the p point is outside the conductor.

[Equation 36]

$$H_{ind}^{(e)}(x_p) = \frac{1}{4\pi}\sum_j \frac{3n(n \cdot m_{ant}^j) - m_{ant}^j}{x_{pj}^3} \quad (Q.22)$$

$C_1$ and $C_2$ are compensation coefficients when compared to a limit expressed as follows in, for example, the expression described in L. D. Landau, E. M. Lifshitz, L. P. Litaevskii, "Electrodynamics of Continuous Media 2nd ed", Jan. 1, 1984, page 205

$$\sqrt{\frac{2}{\mu_0 \sigma \omega}} \gg a \quad \text{[Equation 37]}$$

and take the values of $C_1 = 1/3$ and $C_2 = 3/5$.

The first term (or Q-21-2) on the right side of Q-21 is a term which represents induced magnetization $M_{ant}$ induced in each particle by a time-varying external magnetic field. The second term on the right side of Q-21 and the right side of Q-22 are terms which represent a magnetic field obtained by interaction between magnetic moments $m_{ant}$ based on the induced magnetization of each particle represented by Expression Q-21-4. The induction magnetic field is represented in this way, whereby it is possible to realize dynamic magnetic field analysis in consideration of the influence of the time-varying external magnetic field.

When the renormalization is performed, the electrical conductivity σ is as follows.

$$\sigma' = \sigma a^{\delta/2+1} \quad \text{[Equation 38]}$$

Here, δ=2.

The Lagrange differential on the right side of Q-21-2

$$\frac{\mathcal{D}B_j}{\mathcal{D}t} \quad \text{[Equation 39]}$$

can be replaced with $$\dot{B}_j \quad \text{[Equation 40]}$$

since it is the particle method. It should be noted that transitional movements of magnetization can be considered by movements of particles; however, the rotations of the magnetization vectors should be considered separately (Landau and Lifshitz, Electromagnetism, Chapter 51).

The magnetic field created inside the magnetic body is as follows.

[Equation 41]

$$B(x_p) = \mu_0\left\{H_o(x_p) + \frac{2}{3}M(H)\right\} \quad (Q23)$$

$$H(x_p) = H_o(x_p) - \frac{1}{3}M(H) \quad (Q24)$$

$$\dot{B}(x_p) = \mu_0 \frac{1+\chi(H)}{1+\chi(H)/3}\dot{H}_o(x_p) \quad (Q25)$$

The relationship between the total external field $H_O(x_p)$ and the magnetization $M(H)$ is as follows.

[Equation 42]

$$H_o(x_p) = H_m(x_p) + H_{ext}(x_p) + H_{ind}^{(i)}(x_p) \quad (Q26)$$

$$M(H) = \begin{cases} f(H) & \text{NONLINEAR MATERIAL} \\ 3\left(\frac{\mu-\mu_0}{\mu+2\mu_0}\right)H_o(x_p) & \text{LINEAR MATERIAL} \end{cases} \quad (Q27)$$

By combining Q-26 and Q-27, the magnetic moment $$m_p \quad \text{[Equation 43]}$$

is obtained.

The magnetic field outside the magnetic body is as follows.

[Equation 44]

$$B(x_p) = \mu_0 H_o(x_p) \quad (Q27\text{-}1)$$

$$H(x_p) = H_o(x_p) \quad (Q27\text{-}2)$$

$$\dot{B}(x_p) = \mu_0 \dot{H}_o(x_p) \quad (Q27\text{-}3)$$

$$H_o(x_p) = H_m(x_p) + H_{ext}(x_p) + H_{ind}^{(e)}(x_p) \quad (Q27\text{-}4)$$

Nonlinear Magnetization and Hysteresis
The Magnetic Field $$H \quad \text{[Equation 45]}$$

is removed from Q-27 and Q-24.

[Equation 46]

$$M = f\left(H_o - \frac{1}{3}M\right), \text{ for only sphere} \quad (Q\cdot 28)$$

Figure 9:
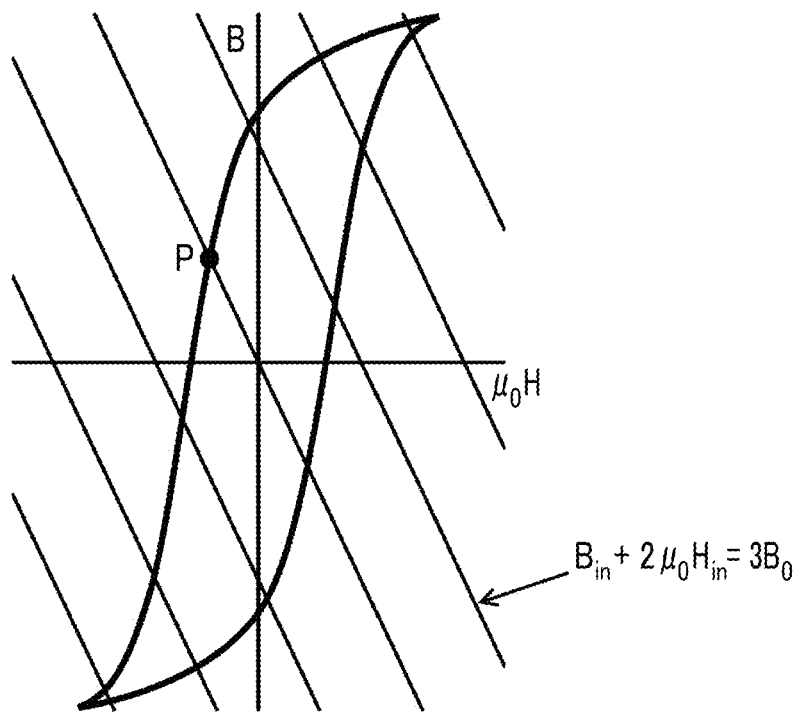
FIG. 9 is a diagram showing a hysteresis curve.

By solving Q-28, the following expression is defined (FIG. 9 shows the case where $B=f(H)$).

$$M = g(H_o) \quad \text{[Equation 47]}$$

FIG. 9 is a diagram showing a hysteresis curve. M is obtained from a point of intersection of the hysteresis curve and $B+2\mu_o H=3B_o$. Now, the permanent magnetization is expressed as follows.

$$M_c \quad \text{[Equation 48]}$$

The B-H curve with the above permanent magnetization is given as follows.

$$B=\mu_o(M_c+\alpha H), \alpha<1. \quad \text{[Equation 49]}$$

This can be combined with $$B+2\mu_o H=\mu_o H_o \quad \text{[Equation 50]}$$

to obtain the following expression.

[Equation 51]

$$M = \frac{3}{2+a}\{M_c - (1-a)H_o\}$$

With regard to a general $B=f(H)$, the Newton-Laphson method is used.

Particulation Method of Magnetic Field

Q-19 is slow to converge since the matrix is not a superdiagonal angle (j=p is excluded). Thus, a solution is obtained from the following equation of motion.

[Equation 52]

$$\mathcal{L}_{EM} = \sum_i \left[\frac{\mu_o}{2}m_v(\dot{H}_{oi}\cdot\dot{H}_{oi}) - \frac{\mu_o}{2}\{H_{oi}-H_o(x_i)\}^2\right] \quad (Q\cdot 29)$$

$$m_v\frac{d\dot{H}_{oi}}{dt} = -[H_{oi} - H_o(x_p)] \quad (Q\cdot 30)$$

Here, $H_O(x_p)$ is represented by Q-26. Furthermore, $m_v$ is a virtual mass. The recommended value is 250×dt×dt. A sufficiently small $m_v$ can induce minute attenuation vibration around the true solution, whereby errors can be reduced.

A model is considered.

[Equation 53]

$$m_v\frac{d\dot{H}}{dt} = -k\{H - H_o\cos(wt)\} - \gamma\dot{H}$$

A solution of forced vibration having an attenuation term (Landau and Lifshitz, Mechanics, Sec. 26) is as follows.

[Equation 54]

$$H = ae^{-\lambda t}\cos(\omega_c t + \alpha) + b\cos(\omega t + \delta), \quad (Q\cdot 32)$$

$$\lambda = \frac{\gamma}{2m}, \omega_o = \sqrt{\frac{k}{m_v}}, \omega_c = \sqrt{\omega_o^2 - \lambda^2}, \quad (Q\cdot 33)$$

$$b = \frac{kH_o/m_v}{\sqrt{(\omega_o^2-\omega^2)^2 + 4\lambda^2\omega^2}}, \tan\delta = \frac{2\lambda\omega}{\omega^2-\omega_o^2} \quad (Q\cdot 34)$$

If the following condition is considered, $$\omega\ll\omega_o,\omega\ll\lambda \quad \text{[Equation 55]}$$

the following expressions are defined.

[Equation 56]

$$H = b\cos(wt+\delta), \quad (Q\cdot 35)$$

$$b = \frac{kH_o}{\sqrt{k^2+\gamma^2\omega^2}}, \tan\delta = -\frac{\gamma}{k}\omega \quad (Q\cdot 36)$$

That is, if $m_v$ is sufficiently small, the solution matches the solution of the following essential equation to be solved.

$$\gamma \dot{H} = -k\{H - H_o \cos(\omega t)\} \qquad \text{[Equation 57]}$$

Discretization

If the discretization is performed according to the leapfrog method (the speed is evaluated at an intermediate point between n and n+1), the following expressions are defined where the number of convergences is s.

[Equation 58]

$$m_v \frac{\dot{H}_{oi}^{n+1/2} - \dot{H}_{oi}^{n-1/2}}{\delta t} = -[H_{oi}^n - H_o^n(x_i)] \qquad (Q\cdot 37\text{-}1)$$

$$\dot{H}_{oi}^{s+1} = \dot{H}_{oi}^s + err, \qquad (Q\cdot 37\text{-}2)$$

$$err = -\dot{H}_{oi}^s + \dot{H}_{oi}^{n-1/2} - \frac{\delta t}{m_v}[H_{oi}^n - H_o^n(x_i)] \qquad (Q\cdot 37\text{-}3)$$

Here, in the discretization of the induction magnetic field $H_{ind}(x_i)$, the following expression is defined.

[Equation 59]

$$\dot{B}^n = \frac{\mu_0}{2}(\dot{H}_o^s + \dot{H}_o^{n-1/2}) \qquad (Q\cdot 38)$$

In this case, if only diagonal elements use further values, an explicit solution is possible and the efficiency will be improved by about 30%. Most of the calculation is calls for special functions.

Acceleration Based on FIRE: Effective Only to Magnetostatic Field Analysis

It is possible to realize further acceleration with an addition of FIRE (see Erik Bitzek et al., "Structural Relaxation Made Simple", Physical Review Letters, Oct. 27, 2006, 97). The code of the FIRE is shown below. The calculation result is 10.05 [s] under the condition that the number of particles is 802 and the residual is <$10^{-8}$. The residual does not fall below $10^{-5}$ without the FIRE.

Ordinary Step (Q•39)
Calculate H, force, and $\dot{H}$ from Eq. (Q•30) (Q•40)
Fire Step (Q•41)

P=force·$\dot{H}$;

$\dot{m}_a = |\dot{H}|, f_a = |\text{force}| + DBL\_MIN$;

$$\dot{H} = \dot{H}(1.0-\alpha) + (\text{force}/f_a)\dot{H}_a\alpha; \qquad \text{[Equation 60]}$$

if (P>0.0) n++;
if (n>5){α=0.99α;n=0;}
if (P<=0.0){$\dot{H}$=0.0;α=0.1;n=0;}

Accuracy Verification: Uniform Magnetization of Sphere

Figure 10:
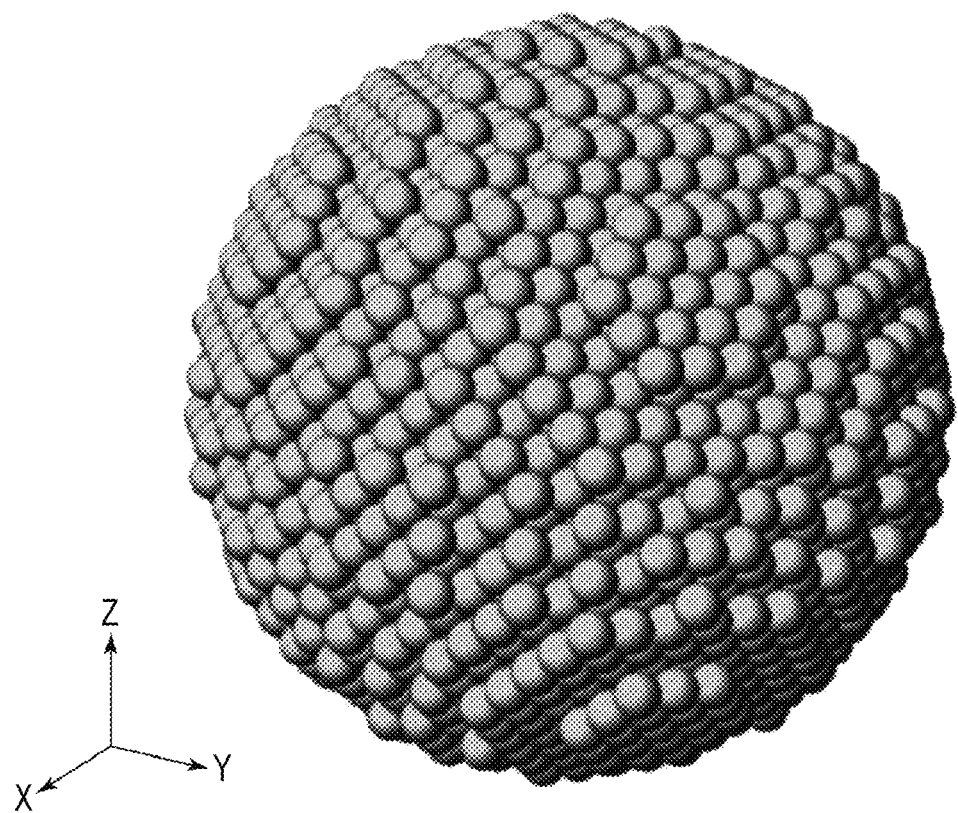
FIG. 10 is a diagram showing an analysis model of a conductive sphere having beads.

FIG. 10 is a diagram showing an analysis model of a conductive sphere having beads. In the accuracy verification, a uniform external magnetic field was applied in a space to be $H_{ext,x} = H_O \sin(2\pi ft)$ in the x axis direction. Here, $H_O = 7.958 \times 10^4$ [A/m], f=200 [Hz], the radius of the conductive sphere A=10 [mm], and electrical conductivity $\sigma = 59 \times 10^6$ [S/m]. The number of particles (atoms) forming the conductive sphere was 6099 and the particles were arranged in an fcc structure.

Figure 11:
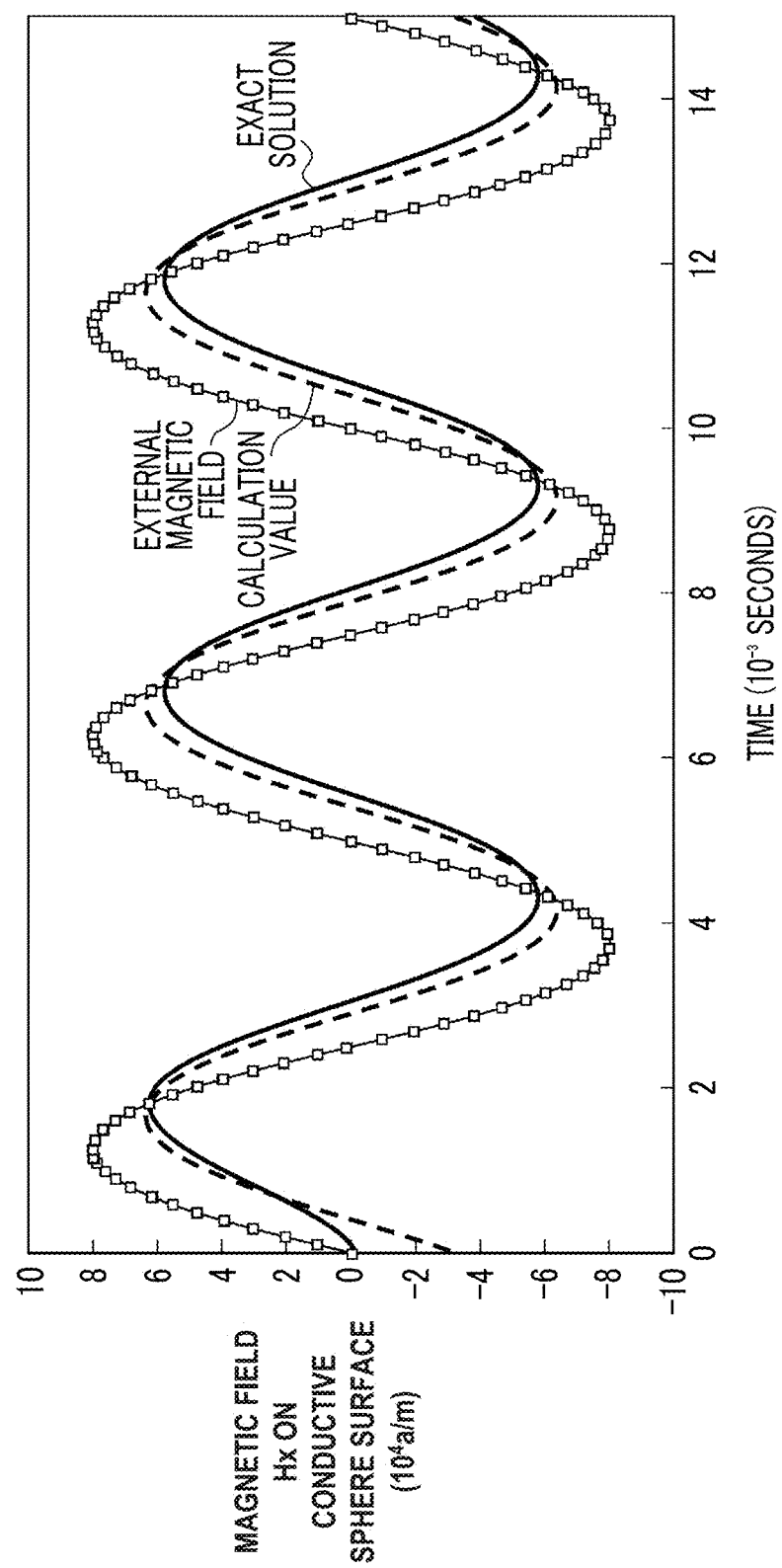
FIG. 11 is a graph showing calculation values of a time-varying magnetic field on a conductive sphere surface.

FIG. 11 is a graph showing calculation values of a time-varying magnetic field on a conductive sphere surface, and shows a time variation in a magnetic field Hx at the gravity center position (rx=9.89 [mm], ry=rz=0) of a particle near a conductor surface. In this drawing, the external magnetic field and the value by the exact solution are shown along with calculation results by a simulation. It is possible to reproduce a form in which the magnetic field inside the conductor changes with a phase delayed with respect to the external magnetic field due to the influence of the induction magnetic field, and it is shown that the calculation result closely matches the tendency of the exact solution.

Figure 12:
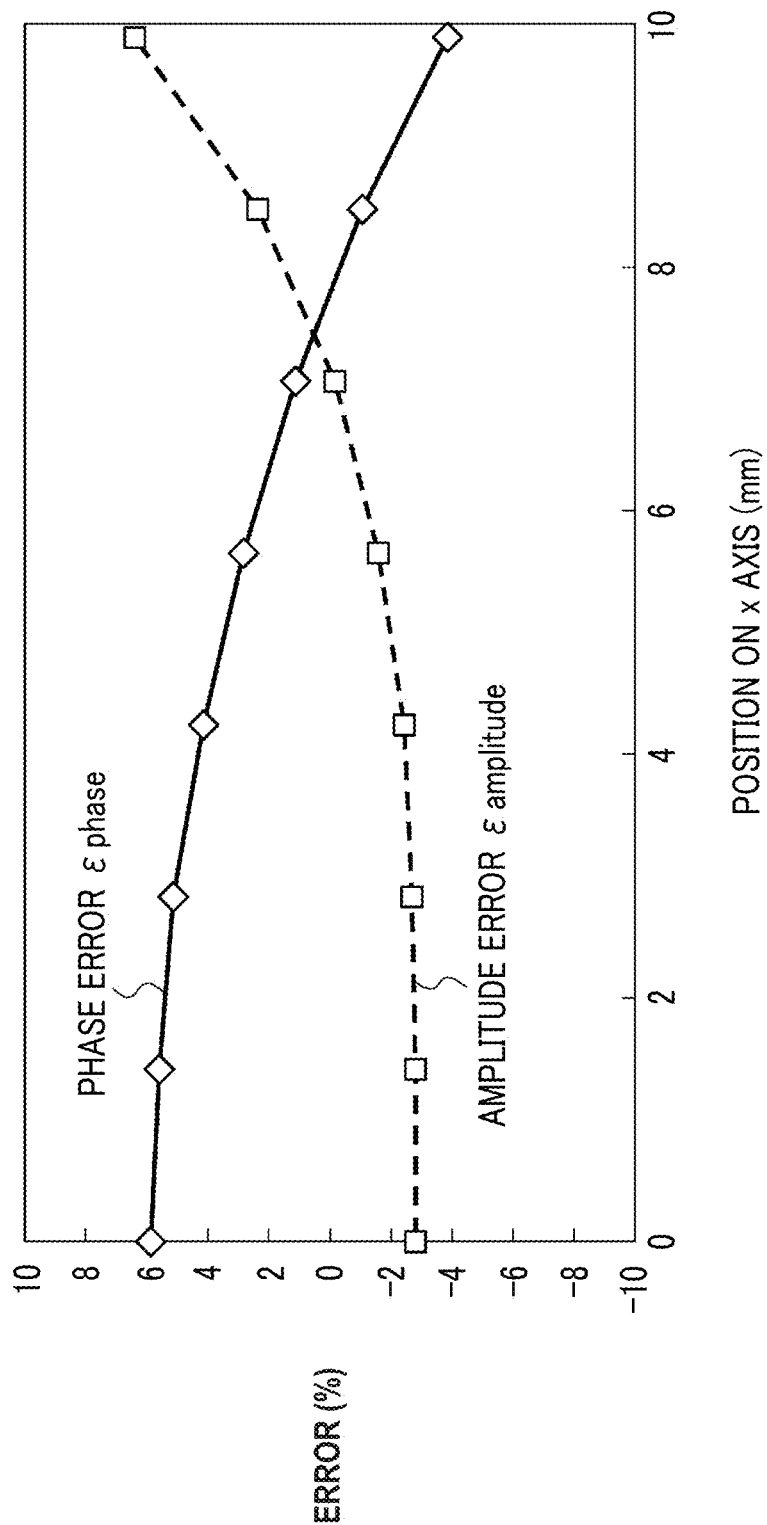
FIG. 12 is a graph showing a phase error and an amplitude error of calculation values.

FIG. 12 is a graph showing a phase error and an amplitude error of calculation values, and shows a phase error $\varepsilon_{phase}$ and an amplitude error $\varepsilon_{amplitude}$ of a magnetic field at the gravity center position of a particle on the x axis. The phase error $\varepsilon_{phase}$ and the amplitude error $\varepsilon_{amplitude}$ are defined as follows.

[Equation 61]

$$\varepsilon_{phase} = \frac{\theta_{exact} - \theta_{MBM}}{2\pi},$$

$$\varepsilon_{amplitude} = \frac{H_{exact} - H_{MBM}}{H_{exact}}$$

Here, $\theta_{exact}$ is a phase of an exact solution, and $\theta_{MBM}$ is a phase of an analysis result. Furthermore, $H_{exact}$ is a magnetic field obtained by the exact solution, and $H_{MBM}$ is a magnetic field of the analysis result. The phase error is obtained by comparing the phase $\theta_{exact}$ when $H_{exact}$ is maximal with the phase $\theta_{MBM}$ when $H_{MBM}$ is maximal. From FIG. 12, the phase error between the analysis result on the x axis and the magnetic field of the exact solution is a maximum of 5.86%, the amplitude error is 6.38%, and it is shown that a high-accuracy analysis result is obtained compared to the exact solution.

Series Representation of Legendre Functions

Special cases of the Legendre functions and the associated Legendre functions are listed below (x:=cos $\theta_j$).

[Equation 62]

$$P_0(x) = 1 \qquad (Q\cdot 42)$$

$$P_1(x) = x \qquad (Q\cdot 43)$$

$$P_2(x) = \frac{1}{2}(3x^2 - 1) \qquad (Q\cdot 44)$$

$$P_3(x) = \frac{1}{2}(5x^3 - 3x) \qquad (Q\cdot 45)$$

$$P_4(x) = \frac{1}{8}(35x^4 - 30x^2 + 3) \qquad (Q\cdot 46)$$

$$P_5(x) = \frac{1}{8}(63x^5 - 70x^2 + 15x) \qquad (Q\cdot 47)$$

and $\qquad (Q\cdot 48)$ $$P_1^1(x) = -(1-x^2)^{1/2} \qquad (Q\cdot 49)$$

$$P_3^1(x) = -\frac{3}{2}(1-x^2)^{1/2}(5x^2-1) \qquad (Q\cdot 50)$$

$$P_3^2(x) = 15(1-x^2)x \qquad (Q\cdot 51)$$

$$P_3^3(x) = -15(1-x^2)^{3/2} \qquad (Q\cdot 52)$$

$$P_5^1(x) = -\frac{1}{8}(1-x^2)^{1/2}(315x^4 - 210x^2 + 15) \qquad (Q\cdot 53)$$

Derivation of Force Applied to Particle

The Lagrangean describing interaction between a particle (electron and nucleus) and a particle magnetic field is as follows.

[Equation 63]

$$\mathcal{L}_{MD} = \sum_{p}^{N}\left[\frac{1}{2}M_p V_p^2 - \Phi(x_p) - eA(x_p)\cdot V_p\right] + \sum_{e}^{N}\left[\frac{1}{2}m_e v_e^2 + eA(x_e)\cdot v_e\right]$$

The relationship between the vector potential $A$ [Equation 64]

and an electromagnetic field is expressed as follows.

[Equation 65]

$$B = \nabla \times A,$$
$$E = -\frac{\partial A}{\partial t}$$

If the following relationship is used,

[Equation 66]

$$\frac{dA}{dt} = \frac{\partial A}{\partial t} + (v_i \cdot \nabla)A,$$
$$\nabla(v_i \cdot A) = (v_i \cdot \nabla)A + v_i \times \nabla \times A$$

the following equation of motion is obtained.

[Equation 67]

$$m_e \frac{dv_e}{dt} = ev_e \times B + eE \text{ for electron}$$
$$M_p \frac{dV_p}{dt} = -eV_p \times B - eE - \nabla\Phi(x_p) \text{ for nucleus}$$

The equation of motion for an atom $M=M_p+m_e$ is as follows.

[Equation 68]

$$M\frac{dV}{dt} = e(v_e - V_p) \times B(x_i) - \nabla\Phi(x_i) - e((x_e - x_p)\cdot\nabla)E(x_i), \quad (R.3)$$
$$x_i = \frac{m_e x_e + M_p x_p}{M_p + m_e}$$

With regard to the right side of the equation, by replacing the Lorentz force with an average current density $j$ [Equation 69]

and replacing the electric moment with $p_e$ [Equation 70], the following expression is defined.

[Equation 71]

$$M\frac{dV_i}{dt} = j \times B(x_i)\delta V_i - (p_e \cdot \nabla)E - \nabla\Phi(x_i) \quad (R.4)$$

From the Maxwell's equation and Q-24,

[Equation 72]

$$j = \nabla \times H, \quad H = \begin{cases} H_o - \frac{1}{3}M(H) & \text{NONLINER MATERIAL} \\ \frac{3\mu_o}{\mu + 2\mu_o}H_o & \text{LINEAR MATERIAL} \end{cases}$$

the force applied to the atom in the end is as follows if electric polarization is neglected.

[Equation 73]

$$f(x_i) = (\nabla \times H) \times B(x_i)\delta V_i - \nabla\Phi(x_i) \quad (R\cdot 5)$$

The force applied to the particle is obtained directly from the Maxwell's stress tensor.

[Equation 74]

$$f_\alpha = \frac{\partial}{\partial x_\beta}T^{\alpha\beta} = [\nabla \times H \times B]_\alpha \quad (R.6)$$

$$T_{\alpha\beta} = \frac{1}{\mu_o}B_\alpha B_\beta - \frac{1}{2\mu_o}B\cdot B\delta_{\alpha\beta} \quad (R.7)$$

The moment created by a localized current at the sphere is expressed as follows.

$m$ [Equation 75]

The force applied to the moment is as follows to the smallest order.

$$f = (m \times \nabla) \times B = \nabla(m\cdot B) - m(\nabla\cdot B) = \nabla(m\cdot B) \quad \text{[Equation 76]}$$

Therefore, the potential energy is expressed as follows together with the potential energy due to electric polarization.

$$U = -m\cdot B + p_e \cdot E \quad \text{[Equation 77]}$$

This does not include an eddy current or a true current.

[Equation 78]

$$j = \nabla \times \left(H_o - \frac{1}{3}M\right) \quad (R.8)$$
$$= \nabla \times H_o - \frac{1}{3}\frac{dM(H)}{dH}\nabla \times H \quad (R.9)$$
$$\therefore j = \frac{1}{1+\chi/3}\nabla \times H_o \quad (R.10)$$
$$\quad (R.11)$$

As a result, by calculating $\nabla \times H_o$ [Equation 79], the magnetic force applied to the magnetic sphere is obtained.

Current Due to Magnetization
Although it is difficult to completely separate $$j_m \quad \text{[Equation 80]}$$

and the eddy current $$j_{eddy} \quad \text{[Equation 81]},$$

the following expressions are respectively defined.

[Equation 82]

$$j_m(x_p) = \frac{1}{1+\mathcal{X}/3} \nabla \times H_m \quad (R.12)$$

$$j_{eddy}(x_p) = \frac{1}{1+\mathcal{X}/3} \nabla \times H_{eddy} \quad (R.13)$$

Calculation of Differential Coefficients
The following is the required differential coefficients. Based on the following expressions,

[Equation 83]

$$\frac{d}{d\cos\theta} P_{2n+1}(\cos\theta) = -\frac{1}{\sin\theta} P^1_{2n+1}(\cos\theta) \quad (R.14)$$

$$\frac{d}{d\cos\theta} P^1_{2n+1}(\cos\theta) = \cot\theta P^1_{2n+1}(\cos\theta) - \frac{1}{\sin\theta} P^2_{2n+1}(\cos\theta) \quad (R.15)$$

$$\frac{\partial}{\partial r}\left(\frac{r^{2n+1}_<}{r^{2n+2}_>}\right) = \begin{cases} -(2n+2)\dfrac{a^{2n+1}}{r^{2n+3}} & r>a \\ (2n+1)\dfrac{r^{2n}}{a^{2n+2}} & r<a \end{cases} \quad (R.16)$$

$$\frac{\partial}{\partial r}\begin{cases} \dfrac{1}{r^3}\left(\dfrac{a}{r}\right)^{2n} & r>a \\ -\left(\dfrac{2n+2}{2n+1}\right)\dfrac{1}{a^3}\left(\dfrac{r}{a}\right)^{2n} & r<a \end{cases} = \begin{cases} -(2n+3)\dfrac{1}{r^4}\left(\dfrac{a}{r}\right)^{2n} & r>a \\ -2n\left(\dfrac{2n+2}{2n+1}\right)\dfrac{1}{a^4}\left(\dfrac{r}{a}\right)^{2n-1} & r<a \end{cases} \quad (R.17)$$

listing of only $r_{pj}>a$ (here, since $$P_{2n+1}{}^1, P_{2n+1}{}^2 \quad \text{[Equation 84]}$$

is proportional to $\sin\theta$, there is no divergence at $\theta=0$) defines the following expressions.

[Equation 85]

$$\frac{\partial H_r(r_{pj})}{\partial r_{pj}} = \quad (R.18)$$

$$-\frac{m_{jz}}{\pi}\sum_{n=0}^{\infty}\frac{(-1)^n(2n+1)!!(n+1)}{2^n n!}\frac{1}{r^4_{pj}}\left(\frac{a}{r_{pj}}\right)^{2n} P_{2n+1}(\cos\theta_{pj})$$

$$\frac{\partial H_r(r_{pj})}{r_{pj}\partial\cos\theta_{pj}} = -\frac{m_{jz}}{2\pi}\sum_{n=0}^{\infty}\frac{(-1)^n(2n+1)!!}{2^n n!}\frac{1}{r^4_{pj}}\left(\frac{a}{r_{pj}}\right)^{2n}\frac{P^1_{2n+1}(\cos\theta_{pj})}{\sin\theta_{pj}} \quad (R.19)$$

$$\frac{\partial H_\theta(r_{pj})}{\partial r_{pj}} = \quad (R.20)$$

$$\frac{m_{jz}}{4\pi}\sum_{n=0}^{\infty}\frac{(-1)^n(2n+1)!!(2n+3)}{2^n(n+1)!}\frac{1}{r^4_{pj}}\left(\frac{a}{r_{pj}}\right)^{2n} P^1_{2n+1}(\cos\theta_{pj})$$

-continued $$\frac{\partial H_\theta(r_{pj})}{r_{pj}\partial\cos\theta_{pj}} = \quad (R.21)$$

$$-\frac{m_{jz}}{4\pi}\sum_{n=0}^{\infty}\frac{(-1)^n(2n+1)!!}{2^n(n+1)!}\frac{1}{r^4_{pj}}\left(\frac{a}{r_{pj}}\right)^{2n}\left[\cot\theta_{pj}P^1_{2n+1} - \frac{P^2_{2n+1}(\cos\theta_{pj})}{\sin\theta_{pj}}\right]$$

$$\frac{\partial H_r(r_{pj},\theta_{pj})}{\partial x_p} = \frac{\partial H_r}{\partial r_{pj}}\frac{x_{pj}}{r_{pj}} - \frac{\partial H_r}{r_{pj}\partial\cos\theta_{pj}}\frac{x_{pj}z_{pj}}{r^2_{pj}} \quad (R.22)$$

[Equation 86]

$$\frac{\partial H_r(r_{pj},\theta_{pj})}{\partial y_p} = \frac{\partial H_r}{\partial r_{pj}}\frac{y_{pj}}{r_{pj}} - \frac{\partial H_r}{r_{pj}\partial\cos\theta_{pj}}\frac{y_{pj}z_{pj}}{r^2_{pj}} \quad (R.23)$$

$$\frac{\partial H_r(r_{pj},\theta_{pj})}{\partial z_p} = \frac{\partial H_r}{\partial r_{pj}}\frac{z_{pj}}{r_{pj}} + \frac{\partial H_r}{r_{pj}\partial\cos\theta_{pj}}\left(1 - \frac{x_{pj}z_{pj}}{r^2_{pj}}\right) \quad (R.24)$$

$$\frac{\partial H_\theta(r_{pj},\theta_{pj})}{\partial x_p} = \frac{\partial H_\theta}{\partial r_{pj}}\frac{x_{pj}}{r_{pj}} - \frac{\partial H_\theta}{r_{pj}\partial\cos\theta_{pj}}\frac{x_{pj}z_{pj}}{r^2_{pj}} \quad (R.25)$$

$$\frac{\partial H_\theta(r_{pj},\theta_{pj})}{\partial y_p} = \frac{\partial H_\theta}{\partial r_{pj}}\frac{y_{pj}}{r_{pj}} - \frac{\partial H_\theta}{r_{pj}\partial\cos\theta_{pj}}\frac{y_{pj}z_{pj}}{r^2_{pj}} \quad (R.26)$$

$$\frac{\partial H_\theta(r_{pj},\theta_{pj})}{\partial z_p} = \frac{\partial H_\theta}{\partial r_{pj}}\frac{z_{pj}}{r_{pj}} + \frac{\partial H_\theta}{r_{pj}\partial\cos\theta_{pj}}\left(1 - \frac{x_{pj}z_{pj}}{r^2_{pj}}\right) \quad (R.27)$$

Calculation of Magnetization Current Created by Magnetic Moment when the Magnetization is Parallel to the Z Axis
The following is the magnetic field when the magnetization is parallel to the z axis.

[Equation 87]

$$\rho_{pj} = \sqrt{x^2_{pj} + y^2_{pj}}, \cos\theta_{pj} = z_{pj}/r_{pj} \quad (R.28)$$

$$H_x(r_{pj}; m_{jz}) = \left\{H_r(r_{pj}; m_z)\frac{\rho_{pj}}{r_{pj}} + H_\theta(r_{pj}; m_z)\frac{z_{pj}}{r_{pj}}\right\}\frac{x_{pj}}{\rho_{pj}} \quad (R.29)$$

$$H_y(r_{pj}; m_{jz}) = \left\{H_r(r_{pj}; m_z)\frac{\rho_{pj}}{r_{pj}} + H_\theta(r_{pj}; m_z)\frac{z_{pj}}{r_{pj}}\right\}\frac{y_{pj}}{\rho_{pj}} \quad (R.30)$$

$$H_z(r_{pj}; m_{jz}) = H_r(r_{pj}; m_z)\frac{z_{pj}}{r_{pj}} - H_\theta(r_{pj}; m_z)\frac{\rho_{pj}}{r_{pj}} \quad (R.31)$$

The magnetization current is expressed as follows.

$$j_m \quad \text{[Equation 88]}$$

Then, the magnetic force created by the magnetization $$f(r_{pj})_m \quad \text{[Equation 89]}$$

is $$f_m(r_{pj}) = j_m \times B \quad \text{[Equation 90]}$$

At first, $$j_m(r_{pj}) \quad \text{[Equation 91]}$$

is obtained.

[Equation 92]

$$j^x(r_{pj}, m_{jz}) = \frac{1}{1+\mathcal{X}/3}\left\{\frac{\partial H^z_m}{\partial y_p} - \frac{\partial H^y_m}{\partial z_p}\right\} \quad (R.32)$$

-continued $$\frac{\partial H_z}{\partial y_p} = \frac{1}{r_{pj}} \left[ \begin{array}{l} \frac{\partial H_r(r_{pj}; m_{jz})}{\partial y_p} z_{pj} - H_r(r_{pj}; m_{jz}) \frac{y_{pj} z_{pj}}{r_{pj}^2} - \\ \frac{\partial H_\theta(r_{pj}; m_{jz})}{\partial y_p} \rho_{pj} - H_\theta(r_{pj}; m_{jz}) y_{pj} \left( \frac{1}{\rho_{pj}} - \frac{\rho_{pj}}{r_{pj}^2} \right) \end{array} \right] \quad \text{(R.32-1)}$$

$$\frac{\partial H_y}{\partial z_p} = \frac{y_{pj}}{r_{pj}} \left[ \begin{array}{l} \frac{\partial H_r(r_{pj}; m_{jz})}{\partial z_p} - H_r(r_{pj}; m_{jz}) \frac{z_{pj}}{r_{pj}^2} + \\ \frac{\partial H_\theta(r_{pj}; m_{jz})}{\partial z_p} \frac{z_{pj}}{\rho_{pj}} + H_\theta(r_{pj}; m_{jz}) \frac{1}{\rho_{pj}} \left( 1 - \frac{z_{pj}^2}{r_{pj}^2} \right) \end{array} \right] \quad \text{(R.32-2)}$$

$$j^y(r_{pj}, m_{jz}) = \frac{1}{1 + \mathcal{X}/3} \left\{ \frac{\partial H_m^x}{\partial z_p} - \frac{\partial H_m^z}{\partial x_p} \right\} \quad \text{(R.33)}$$

$$\frac{\partial H_x}{\partial z_p} = \frac{x}{r_{pj}} \left[ \begin{array}{l} \frac{\partial H_r(r_{pj}; m_{jz})}{\partial z_p} - H_r(r_{pj}; m_{jz}) \frac{z_{pj}}{r_{pj}^2} + \\ \frac{\partial H_\theta(r_{pj}; m_{jz})}{\partial z_p} \frac{z_{pj}}{\rho_{pj}} + H_\theta(r_{pj}; m_{jz}) \frac{1}{\rho_{pj}} \left( 1 - \frac{z_{pj}^2}{r_{pj}^2} \right) \end{array} \right] \quad \text{(R.33-1)}$$

$$\frac{\partial H_z}{\partial x_p} = \frac{1}{r_{pj}} \left[ \begin{array}{l} \frac{\partial H_r(r_{pj}; m_{jz})}{\partial x_p} z_{pj} - H_r(r_{pj}; m_{jz}) \frac{x_{pj} z_{pj}}{r_{pj}^2} - \\ \frac{\partial H_\theta(r_{pj}; m_{jz})}{\partial x_p} \rho_{pj} - H_\theta(r_{pj}; m_{jz}) x_{pj} \left( \frac{1}{\rho_{pj}} - \frac{\rho_{pj}}{r_{pj}^2} \right) \end{array} \right] \quad \text{(R.33-2)}$$

$$j^z(r_{pj}, m_{jz}) = \frac{1}{1 + \mathcal{X}/3} \left\{ \frac{\partial H_m^y}{\partial x_p} - \frac{\partial H_m^x}{\partial y_p} \right\} \quad \text{(R.34)}$$

$$\frac{\partial H_x}{\partial y_p} = \frac{x_{pj}}{r_{pj}} \left[ \begin{array}{l} \frac{\partial H_r(r_{pj}; m_{jz})}{\partial y_p} - H_r(r_{pj}; m_{jz}) \frac{y_{pj}}{r_{pj}^2} + \\ \frac{\partial H_\theta(r_{pj}; m_{jz})}{\partial y_p} \frac{z_{pj}}{\rho_{pj}} - H_\theta(r_{pj}; m_{jz}) \frac{y_{pj} z_{pj}}{\rho_{pj}} \left( \frac{1}{r_{pj}^2} + \frac{1}{\rho_{pj}^2} \right) \end{array} \right] \quad \text{(R.34-1)}$$

$$\frac{\partial H_y}{\partial x_p} = \quad \text{(R.34-2)}$$
$$+ \frac{y_{pj}}{r_{pj}} \left[ \begin{array}{l} \frac{\partial H_r(r_{pj}; m_{jz})}{\partial x_p} - H_r(r_{pj}; m_{jz}) \frac{x_{pj}}{r_{pj}^2} + \\ \frac{\partial H_\theta(r_{pj}; m_{jz})}{\partial x_p} \frac{z_{pj}}{\rho_{pj}} - H_\theta(r_{pj}; m_{jz}) \frac{x_{pj} z_{pj}}{\rho_{pj}} \left( \frac{1}{r_{pj}^2} + \frac{1}{\rho_{pj}^2} \right) \end{array} \right]$$

When the Magnetization is Parallel to the x Axis

The following is the magnetic field when the magnetization is parallel to the x axis.

[Equation 93]

$$\rho_{pj} = \sqrt{y_{pj}^2 + z_{pj}^2}, \cos\theta_{pj} = x_{pj}/r_{pj} \quad \text{(R.34)}$$

[Equation 94]

$$H_x(r_{pj}, m_{jx}) = H_r(r_{pj}; m_x) \frac{x_{pj}}{r_{pj}} - H_\theta(r_{pj}; m_x) \frac{\rho_{pj}}{r_{pj}} \quad \text{(R.35)}$$

$$H_y(r_{pj}, m_{jx}) = \left\{ H_r(r_{pj}; m_x) \frac{\rho_{pj}}{r_{pj}} + H_\theta(r_{pj}; m_x) \frac{x_{pj}}{r_{pj}} \right\} \frac{y_{pj}}{\rho_{pj}} \quad \text{(R.36)}$$

$$H_z(r_{pj}, m_{jx}) = \left\{ H_r(r_{pj}; m_x) \frac{\rho_{pj}}{r_{pj}} + H_\theta(r_{pj}; m_x) \frac{x_{pj}}{r_{pj}} \right\} \frac{z_{pj}}{\rho_{pj}} \quad \text{(R.37)}$$

The magnetization current $$j_{m_x} \quad \text{[Equation 95]}$$

is obtained.

[Equation 96]

$$j^x(r_{pj}, m_{jx}) = \frac{1}{1 + \mathcal{X}/3} \left\{ \frac{\partial H_m^z}{\partial y_p} - \frac{\partial H_m^y}{\partial z_p} \right\} \quad \text{(R.38)}$$

$$\frac{\partial H_z}{\partial y_p} = \frac{z_{pj}}{r_{pj}} \left[ \begin{array}{l} \frac{\partial H_r(r_{pj}; m_{jx})}{\partial y_p} - H_r(r_{pj}; m_{jx}) \frac{z_{pj}}{r_{pj}^2} + \\ \frac{\partial H_\theta(r_{pj}; m_{jx})}{\partial y_p} \frac{x_{pj}}{\rho_{pj}} - H_\theta(r_{pj}; m_{jx}) \frac{x_{pj} y_{pj}}{\rho_{pj}} \left( \frac{1}{r_{pj}^2} + \frac{1}{\rho_{pj}^2} \right) \end{array} \right] \quad \text{(R.38-1)}$$

$$\frac{\partial H_y}{\partial z_p} = \quad \text{(R.38-2)}$$
$$\frac{y_{pj}}{r_{pj}} \left[ \begin{array}{l} \frac{\partial H_r(r_{pj}; m_{jx})}{\partial z_p} - H_r(r_{pj}; m_{jx}) \frac{z_{pj}}{r_{pj}^2} + \\ \frac{\partial H_\theta(r_{pj}; m_{jx})}{\partial z_p} \frac{x_{pj}}{\rho_{pj}} - H_\theta(r_{pj}; m_{jx}) \frac{x_{pj} z_{pj}}{\rho_{pj}^x} z_{pj} \left( \frac{1}{r_{pj}^2} + \frac{1}{\rho_{pj}^2} \right) \end{array} \right]$$

$$j^y(r_{pj}, m_{jx}) = \frac{1}{1 + \mathcal{X}/3} \left\{ \frac{\partial H_m^x}{\partial z_p} - \frac{\partial H_m^z}{\partial x_p} \right\} \quad \text{(R.39)}$$

$$\frac{\partial H_x}{\partial z_p} = \frac{1}{r_{pj}} \left[ \begin{array}{l} \frac{\partial H_r(r_{pj}; m_{jx})}{\partial z_p} x_{pj} - H_r(r_{pj}; m_{jx}) \frac{x_{pj} z_{pj}}{r_{pj}^2} - \\ \frac{\partial H_\theta(r_{pj}; m_{jx})}{\partial z_p} \rho_{pj} - H_\theta(r_{pj}; m_{jx}) z_{pj} \left( \frac{1}{\rho_{pj}} - \frac{\rho_{pj}}{r_{pj}^2} \right) \end{array} \right] \quad \text{(R.39-1)}$$

$$\frac{\partial H_z}{\partial x_p} = \frac{1}{r_{pj}} \left[ \begin{array}{l} \frac{\partial H_r(r_{pj}; m_{jx})}{\partial x_p} z_{pj} + H_r(r_{pj}; m_{jx}) \left( 1 - \frac{x_{pj} z_{pj}}{r_{pj}^2} \right) + \\ \frac{\partial H_\theta(r_{pj}; m_{jx})}{\partial x_p} \frac{x_{pj} z_{pj}}{\rho_{pj}} + H_\theta(r_{pj}; m_{jx}) \frac{z_{pj}}{\rho_{pj}} \left( 1 - \frac{x_{pj}^2}{r_{pj}^2} \right) \end{array} \right] \quad \text{(R.39-2)}$$

$$j^z(r_{pj}, m_{jx}) = \frac{1}{1 + \mathcal{X}/3} \left\{ \frac{\partial H_m^y}{\partial x_p} - \frac{\partial H_m^x}{\partial y_p} \right\} \quad \text{(R.40)}$$

$$\frac{\partial H_x}{\partial y_p} = \frac{1}{r_{pj}} \left[ \begin{array}{l} \frac{\partial H_r(r_{pj}; m_{jx})}{\partial y_p} x_{pj} - H_r(r_{pj}; m_{jx}) \frac{x_{pj} y_{pj}}{r_{pj}^2} - \\ \frac{\partial H_\theta(r_{pj}; m_{jx})}{\partial y_p} \rho_{pj} - H_\theta(r_{pj}; m_{jx}) y_{pj} \left( \frac{1}{\rho_{pj}} - \frac{\rho_{pj}}{r_{pj}^2} \right) \end{array} \right] \quad \text{(R.40-1)}$$

$$\frac{\partial H_y}{\partial x_p} = \frac{y_{pj}}{r_{pj}} \left[ \begin{array}{l} \frac{\partial H_r(r_{pj}; m_{jx})}{\partial x_p} - H_r(r_{pj}; m_{jx}) \frac{x_{pj}}{r_{pj}^2} + \\ \frac{\partial H_\theta(r_{pj}; m_{jx})}{\partial x_p} \frac{x_{pj}}{\rho_{pj}} + H_\theta(r_{pj}; m_{jx}) \frac{1}{\rho_{pj}} \left( 1 - \frac{x_{pj}^2}{r_{pj}^2} \right) \end{array} \right] \quad \text{(R.40-2)}$$

When the Magnetization is Parallel to the y Axis

The following is the magnetic field when the magnetization is parallel to the y axis.

[Equation 97]

$$\rho_{pj} = \sqrt{x_{pj}^2 + z_{pj}^2}, \cos\theta_{pj} = y_{pj}/r_{pj} \quad \text{(R.41)}$$

$$H_x(r_{pj}, m_{jy}) = \left\{ H_r(r_{pj}; m_y) \frac{\rho_{pj}}{r_{pj}} + H_\theta(r_{pj}; m_y) \frac{y_{pj}}{r_{pj}} \right\} \frac{x_{pj}}{\rho_{pj}} \quad \text{(R.42)}$$

$$H_y(r_{pj}, m_{jy}) = H_r(r_{pj}; m_y) \frac{y_{pj}}{r_{pj}} - H_\theta(r_{pj}; m_y) \frac{\rho_{pj}}{r_{pj}} \quad \text{(R.43)}$$

$$H_z(r_{pj}, m_{jy}) = \left\{ H_r(r_{pj}; m_y) \frac{\rho_{pj}}{r_{pj}} + H_\theta(r_{pj}; m_y) \frac{y_{pj}}{r_{pj}} \right\} \frac{z_{pj}}{\rho_{pj}} \quad \text{(R.44)}$$

The magnetization current $$j_{m_y} \quad \text{[Equation 98]}$$

is obtained.

[Equation 99]

$$j^x(r_{pj}, m_{jy}) = \frac{1}{1+X/3}\left\{\frac{\partial H_m^z}{\partial y_p} - \frac{\partial H_m^y}{\partial z_p}\right\} \quad (\text{R.45})$$

$$\frac{\partial H_z}{\partial y_p} = \frac{z_{pj}}{r_{pj}}\left[\begin{array}{l}\frac{\partial H_r(r_{pj}; m_{jy})}{\partial y_p} - H_r(r_{pj}; m_{jy})\frac{y_{pj}^2}{r_{pj}^2} + \\ \frac{\partial H_\theta(r_{pj}; m_{jy})}{\partial y_p}\frac{y_{pj}}{\rho_{pj}} + H_\theta(r_{pj}; m_{jy})\frac{1}{\rho_{pj}}\left(1 - \frac{y_{pj}^2}{r_{pj}^2}\right)\end{array}\right] \quad (\text{R.45-1})$$

$$\frac{\partial H_y}{\partial z_p} = \frac{1}{r_{pj}}\left[\begin{array}{l}\frac{\partial H_r(r_{pj}; m_{jy})}{\partial z_p}y_{pj} - H_r(r_{pj}; m_{jy})\frac{y_{pj}z_{pj}}{r_{pj}^2} - \\ \frac{\partial H_\theta(r_{pj}; m_{jy})}{\partial z_p}\rho_{pj} - H_\theta(r_{pj}; m_{jy})z_{pj}\left(\frac{1}{\rho_{pj}} - \frac{\rho_{pj}}{r_{pj}^2}\right)\end{array}\right] \quad (\text{R.45-2})$$

$$j^y(r_{pj}, m_{jy}) = \frac{1}{1+X/3}\left\{\frac{\partial H_m^x}{\partial z_p} - \frac{\partial H_m^z}{\partial x_p}\right\} \quad (\text{R.46})$$

$$\frac{\partial H_x}{\partial z_p} = \quad (\text{R.46-1})$$

$$\frac{x_{pj}}{r_{pj}}\left[\begin{array}{l}\frac{\partial H_r(r_{pj}; m_{jy})}{\partial z_p} - H_r(r_{pj}; m_{jy})\frac{z_{pj}}{r_{pj}^2} + \\ \frac{\partial H_\theta(r_{pj}; m_{jy})}{\partial z_p}\frac{y_{pj}}{\rho_{pj}} - H_\theta(r_{pj}; m_{jy})\frac{y_{pj}z_{pj}}{\rho_{pj}}\left(\frac{1}{r_{pj}^2} + \frac{1}{\rho_{pj}^2}\right)\end{array}\right]$$

$$\frac{\partial H_z}{\partial x_p} = \frac{z_{pj}}{r_{pj}}\left[\begin{array}{l}\frac{\partial H_r(r_{pj}; m_{jy})}{\partial x_p} - H_r(r_{pj}; m_{jy})\frac{x_{pj}}{r_{pj}^2} + \\ \frac{\partial H_\theta(r_{pj}; m_{jy})}{\partial x_p}\frac{y_{pj}}{\rho_{pj}} - H_\theta(r_{pj}; m_{jy})\frac{x_{pj}z_{pj}}{\rho_{pj}}\left(\frac{1}{r_{pj}^2} + \frac{1}{\rho_{pj}^2}\right)\end{array}\right] \quad (\text{R.46-2})$$

$$j^z(r_{pj}, m_{jy}) = \frac{1}{1+X/3}\left\{\frac{\partial H_m^y}{\partial x_p} - \frac{\partial H_m^x}{\partial y_p}\right\} \quad (\text{R.47})$$

$$\frac{\partial H_x}{\partial y_p} = \frac{x_{pj}}{r_{pj}}\left[\begin{array}{l}\frac{\partial H_r(r_{pj}; m_{jy})}{\partial y_p} - H_r(r_{pj}; m_{jy})\frac{y_{pj}^2}{r_{pj}^2} + \\ \frac{\partial H_\theta(r_{pj}; m_{jy})}{\partial y_p}\frac{y_{pj}}{\rho_{pj}} + H_\theta(r_{pj}; m_{jy})\frac{1}{\rho_{pj}}\left(1 - \frac{y_{pj}^2}{r_{pj}^2}\right)\end{array}\right] \quad (\text{R.47-1})$$

$$\frac{\partial H_y}{\partial x_p} = \frac{1}{r_{pj}}\left[\begin{array}{l}\frac{\partial H_r(r_{pj}; m_{jy})}{\partial x_p}y_{pj} - H_r(r_{pj}; m_{jy})\frac{x_{pj}y_{pj}}{r_{pj}^2} - \\ \frac{\partial H_\theta(r_{pj}; m_{jy})}{\partial x_p}\rho_{pj} - H_\theta(r_{pj}; m_{jy})x_{pj}\left(\frac{1}{\rho_{pj}} - \frac{\rho_{pj}}{r_{pj}^2}\right)\end{array}\right] \quad (\text{R.47-2})$$

Calculation of Eddy Current Created by Induction Magnetic Field

According to Q-21, the induction magnetic field inside the conductor is defined as follows.

[Equation 100]

$$H_{ind}(x_p) = M_{ant}(x_p) + \frac{1}{4\pi}\sum_j \frac{3n(n \cdot m_{ant}^j) - m_{ant}^j}{x_{pj}^3} \quad (\text{R.48})$$

$$G(x_{pj}) = \begin{cases} \frac{1}{3}\frac{a_j^3}{x_{pj}} & x_{pj} > a_j \\ \frac{a_j^2}{2} - \frac{x_{pj}^2}{6} & x_{pj} < a_j \end{cases} \quad (\text{R.49})$$

$$M_{ant}(x_p) = -C_1 \sum_j \sigma_j G(x_{pj})\frac{\mathcal{D}B_j}{\mathcal{D}t} \quad (\text{R.49-1})$$

$$m_{ant}^j = C_2 M_{ant}(x_j)\delta V_j \quad (\text{R.49-2})$$

The eddy current is as follows.

[Equation 101]

$$j_{eddy}(x_p) = \frac{1}{1+X/3}\nabla \times H_{ind}(x_p) \quad (\text{R.50})$$

$$= \frac{1}{1+X/3}\nabla \times \left[M_{ant}(x_p) + \frac{1}{4\pi}\sum_j \frac{3n(n \cdot m_{ant}^j) - m_{ant}^j}{x_{pj}^3}\right] \quad (\text{R.51})$$

$$\nabla \times M_{ant}(x_p) = -C_1 \sum_j \sigma_j\left[\nabla \times \left\{G(x_{pj})\frac{\mathcal{D}B_j}{\mathcal{D}t}\right\}\right] \quad (\text{R.52-1})$$

$$\nabla \times \left[\frac{1}{4\pi}\sum_j \frac{3n(n \cdot m_{ant}^j) - m_{ant}^j}{x_{pj}^3}\right] \quad (\text{R.52-2})$$

Expression R-52-2 is the same as a case where the expansion order of spherical harmonics n=0 in R-12.

Calculation of Force Applied to Particle

By adding $m_x$, $m_y$, $m_z$, and the contributions from the eddy current, the total current is obtained.

[Equation 102]

$$j(x_p) = \sum_{j \neq p}\{j(r_{pj}, m_x) + j(r_{pj}, m_y) + j(r_{pj}, m_z)\} + j_{eddy}(r_p) \quad (\text{R.53})$$

The force applied to a particle at a coordinate $x_p$ [Equation 103]

is defined as follows.

[Equation 104]

$$f(x_p) = j(x_p) \times B(x_p)\delta V_p - \nabla_p \Phi(r_p) \quad (\text{R·54})$$

In the end, it is necessary to add a term derived from the derivative of the following expression.

$\mathcal{L}_{EM}$ [Equation 105]

This is a virtual force created by an error of the magnetic field $H_{op} - H_o(x_i)$ [Equation 106], and the total energy of the motion and the magnetic field is conserved.

[Equation 107]

$$f(x_p) = j(x_p) \times B(x_p)\delta V_p - \nabla_p\Phi(r_p) + \mu_o$$
$$[\{(H_{op} - H_o(x_p)) \cdot \nabla\}H_o(x_p) - j(x_p) \times$$
$$\{H_{op} - H_o(x_p)\}]\delta V_p \quad (\text{R·55})$$

Another Embodiment

In the above-described embodiment, a case has been described where the dynamic magnetic field analysis is performed using the induced magnetization in the first term on the right side of Q-21 and Expression (Q-21) for the induction magnetic field represented by interaction between magnetic moments in the second term on the right side. In this embodiment, the induction magnetic field is formulated using the exact solution of the vector potential derived from a differential equation of a vector potential, instead of using Expression Q-21. The following description will be provided focusing on the difference from the above-described embodiment.

With regard to a vector potential A, the following differential equation is established.

[Equation 108]

$$\mu\sigma\frac{\partial A(r)}{\partial t} = \nabla^2 A(r) \quad \text{(S-1)}$$

The solution of the differential equation is as follows.

[Equation 109]

$$A(r) = -\frac{\mu}{4\pi}\int d^3r'\frac{\sigma(r')\dot{A}(r')}{|r-r'|} \quad \text{(S-2)}$$

Here, if it is assumed that $$r' = r_j + \rho \quad \text{[Equation 110]},$$

and if an object is divided into particles, the vector potential of each particle at a position $r_i$ is as follows.

[Equation 111]

$$A(r_i) = -\frac{\mu}{4\pi}\sum_{j\subset i}^{N_i}\int_{r_j+v_j}d^3r'\frac{\sigma(r')\dot{A}(r')}{|r-r'|} \quad \text{(S-3)}$$

$$= -\frac{\mu}{4\pi}\sum_{j\subset i}^{N_i}\int_{v_j}d^3\rho\frac{\sigma_j\dot{A}_j(\rho)}{|r_{ij}-\rho|}$$

Here, $v_j$ is a volume of each particle. With regard to the sum of j, when a vector $$r_i - r_j \quad \text{[Equation 112]}$$

crosses the particle surface, the sum is not taken. A condition which should be satisfied by the particle size a is as follows.

$$\sqrt{2/(\mu\sigma\omega)} \gg a \quad \text{[Equation 113]}$$

In this case, the division of each object into particles may cause losing of the transitional symmetry of the vector potential A. Thus, the inventors have found that gauge transformation shown in S-4 is introduced, thereby recovering the transitional symmetry of the vector potential A. In this specification, the gauge transformation is referred to as "beads gauge".

[Equation 114]

$$A_j(\rho) \to A_j(\rho) - \frac{1}{2}B_j \times g_i \quad \text{(S-4)}$$

Here, a vector $g_i$ is a local gravity center vector relating to a particle group (the number of particles: $N_i$) to be calculated and is expressed as follows.

[Equation 115]

$$g_i = \frac{1}{N_i}\sum_{j\subset i}^{N_i}r_j \quad \text{(S-5)}$$

Therefore, the vector $g_i$ represents the gravity center position of the particle group. It can be said that the beads gauge shown in S-4 is described using the outer product of a magnetic flux density $B_j$ and the local gravity center vector $g_i$.

With regard to the beads gauge, the relationship expression of the magnetic flux density B and the vector potential A $$B(r_j) = \nabla \times A_j(\rho) \quad \text{[Equation 116]}$$

is obtained as follows.

[Equation 117]

$$B(r_j) = \left(1 - \frac{1}{N_i}\right)B_j = B_j + O\left(\frac{1}{N_i}\right) \quad \text{(S-6)}$$

Therefore, it can be understood that, if the number of particles $N_i$ is sufficiently large, the transitional symmetry is satisfied.

Here, from the gauge transformation shown in S-4, the time differential of the vector potential included in the right side of S-3

$$\dot{A}_j(\rho) \quad \text{[Equation 118]}$$

can be expressed as follows using the time differential of the magnetic flux density B.

[Equation 119]

$$\dot{A}_j(\rho) = \frac{1}{2}\dot{B}_j \times (d_{ji} + \rho) \quad \text{(S-7)}$$

If a vector $d_{ji}$ is

[Equation 120]

$$d_{ji} = r_j - g_i \quad \text{(S-8)},$$

the time differential of the vector potential is expressed as follows.

[Equation 121]

$$\dot{A}_j(\rho) = \frac{1}{2}\dot{B}_j \times (r_j + \rho) - \frac{1}{2}\dot{B}_j \times g_i \quad \text{(S-9)}$$

Therefore, if integration is executed by substituting S-9 in S-3, the exact solution of the vector potential A can be described using the time differential of the magnetic flux density B.

In order to derive the exact solution of the vector potential A, first, integration when only $$\dot{B}_z \quad \text{[Equation 122]}$$

which is the time differential of the z component of the magnetic flux density B is applied is executed. With this, the vector potential A is

[Equation 123]

$$A(r_i) = \qquad\qquad\qquad\qquad\qquad (S\text{-}10)$$
$$-\frac{\mu}{8\pi}\sum_{j<i}^{N_i}\sigma_j[-\dot{B}_{jz}(y_j-g_{iy}),\dot{B}_{jz}(x_j-g_{ix}),0]\int_{v_j}d^3\rho\frac{1}{|r_{ij}-\rho|}-$$
$$\frac{\mu}{8\pi}\sum_{j<i}^{N_i}\int_{v_j}d^3\rho\frac{\sigma_j[-\dot{B}_{jz}\rho_y,\dot{B}_{jz}\rho_x,0]}{|r_{ij}-\rho|}$$

If the contributions from $$\dot{B}_x,\dot{B}_y \qquad\qquad\qquad\qquad [\text{Equation 124}]$$

which are the time differentials of the x component and the y component of the magnetic flux density B are added, the following expression is obtained.

[Equation 125]

$$A(r_i) = -\frac{\mu}{2}\sum_{j<i}^{N_i}\sigma_j(B_j\times d_{ji})\begin{cases}\frac{1}{3}r_{ij}^2+\frac{1}{2}(a^2-r_{ij}^2) & r_{ij}\le a \\ \frac{1}{3}\frac{a^3}{r_{ij}} & r_{ij}>a\end{cases} \quad (S\text{-}11)$$
$$\frac{\mu}{6}\sum_{j<i}^{N_i}\sigma_j(\dot{B}_j\times r_{ij})\begin{cases}\frac{1}{5}r_{ij}^2+\frac{1}{2}(a^2-r_{ij}^2) & r_{ij}\le a \\ \frac{1}{5}\frac{a^5}{r_{ij}^3} & r_{ij}>a\end{cases}$$

An induction magnetic field H which describes the inside of a conductor to be analyzed from the following relationship expression $$\mu H = B = \nabla\times A \qquad\qquad [\text{Equation 126}]$$

is

[Equation 127]

$$H(r_i) = -\frac{1}{6}\sum_{j<i}^{N_i}\sigma_j\begin{cases}-(r_{ij}\cdot d_{ji})\dot{B}_j+(r_{ij}\cdot\dot{B}_j)d_{ji}+O(1/N_i) & r_{ij}\le a \\ -\frac{a^3}{r_{ij}^3}(r_{ij}\cdot d_{ji})\dot{B}_j+\frac{a^3}{r_{ij}^3}(r_{ij}\cdot\dot{B}_j)d_{ji}+ & r_{ij}>a \\ O(1/N_i)\end{cases} \quad (S\text{-}12)$$
$$-\frac{1}{6}\sum_{j<i}^{N_i}\sigma_j\begin{cases}\left(a^2-\frac{6}{5}r_{ij}^2\right)\dot{B}_j+\frac{3}{5}(r_{ij}\cdot\dot{B}_j)r_{ij} & r_{ij}\le a \\ \frac{a^5}{5r_{ij}^3}\{3(n_{ij}\cdot\dot{B}_j)n_{ij}-\dot{B}_j\} & r_{ij}>a\end{cases}$$
$$\cong -\frac{1}{6}\sigma_i a^2\dot{B}_i - \frac{1}{6}\sum_{j<i}^{N_i}\sigma_j\frac{a^3}{r_{ij}^3}\left[\begin{array}{l}-(r_{ij}\cdot d_{ji})\dot{B}_j+(r_{ij}\cdot\dot{B}_j)d_{ji}+\\ \frac{a^2}{5}\{3(n_{ij}\cdot\dot{B}_j)n_{ij}-\dot{B}_j\}\end{array}\right]$$

Here, by replacing with $$r_j = r_i - r_{ij} \qquad\qquad [\text{Equation 128}]$$

as the expression for the induction magnetic field H,

[Equation 129]

$$H(r_i) = -\frac{a^3}{6}\sum_{j<i}^{N_i}\sigma_j\left[\frac{\dot{B}_j-(n_{ij}\cdot\dot{B}_j)n_{ij}}{r_{ij}} - \frac{(r_{ij}\cdot d_{ii})\dot{B}_j-(r_{ij}\cdot\dot{B}_j)d_{ii}}{r_{ij}^3}\right]- \quad (S\text{-}13)$$
$$\frac{1}{6}\sigma_i a^2\dot{B}_i - \frac{1}{30}\sum_{j<i}^{N_i}\sigma_j a^5\frac{3(n_{ij}\cdot\dot{B}_j)n_{ij}-\dot{B}_j}{r_{ij}^3}$$

is obtained.

The magnetic field calculation unit 121 calculates the induction magnetic field generated by the particle system using the expression for the induction magnetic field shown in S-13. In the calculation for obtaining the time variation value of the induction magnetic field, the same method as in the above-described embodiment should be used. The magnetic field calculation unit 121 may calculate a current density from the obtained induction magnetic field. The force calculation unit 122 may calculate an electromagnetic force from the values of the obtained magnetic field and current.

In this embodiment, the local gravity center vector $g_i$ shown in S-5 is introduced for particle groups at the same potential, and separate local gravity center vectors are introduced for a plurality of particle groups electrically insulated from one another. For example, when a particle system to be analyzed has a plurality of portions electrically insulated from one another, local gravity center vectors having different gravity center positions are applied to particle groups forming the respective portions. When an object to be analyzed is deformed over time and divided into a plurality of objects, and the divided portions are insulated from one another, local gravity center vectors having different gravity center positions are applied to particle groups forming the respective portions.

Accordingly, when a plurality of particle groups including a first particle group and a second particle group electrically insulated from each other are arranged in a particle system to be analyzed, the magnetic field calculation unit 121 performs analysis using an expression for an induction magnetic field corresponding to each particle group. For example, the induction magnetic field in the first particle group is calculated using an expression for a first induction magnetic field derived by gauge transformation using a first local gravity center vector representing the gravity center position of the first particle group. The induction magnetic field in a second particle group is calculated using an expression for a second induction magnetic field derived by gauge transformation using a second local gravity center vector representing the gravity center position of the second particle group. Specifically, in the expression for the induction magnetic field shown in S-13, $d_{ij}$ included in the first term on the right side takes a different value in the calculation of each particle group.

Accuracy verification was performed for an analysis method using Expression (S-13) for an induction magnetic field according to this embodiment. As in the above-described embodiment, an analysis model of a conductive sphere shown in FIG. 10 was used, and a uniform external magnetic field was applied in a space to be $H_{ext,x} = H_O \sin(2\pi ft)$ in the x-axis direction. Calculation conditions were $H_O = 7.948\times 10^4$ [A/m], f=100 [Hz], the radius of the conductive sphere A=10 [mm], and electrical conductivity σ=59×10⁶ [S/m]. The number of particles (atoms) forming the conductive sphere was 6099 and the particles were arranged in an fcc structure.

Figure 13A:
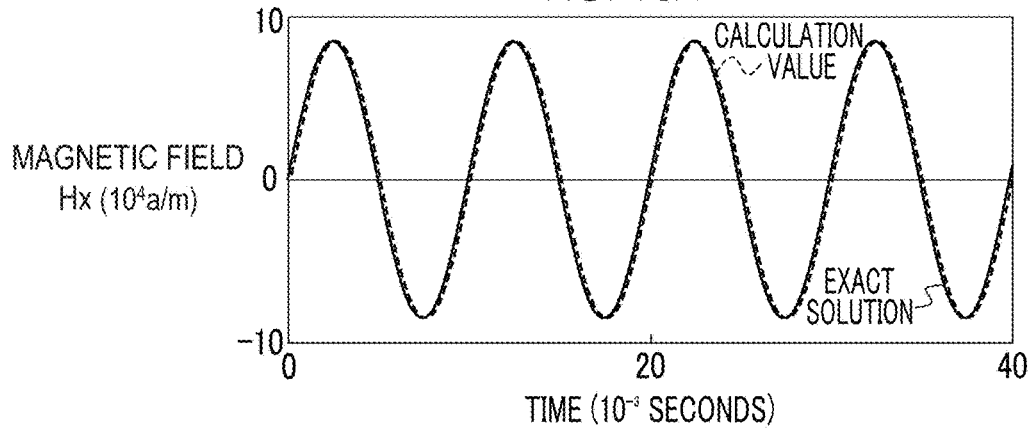
FIGS. 13A to 13C are graphs showing calculation values of a magnetic field on a conductive sphere surface, current density, and an electromagnetic force.
Figure 13B:
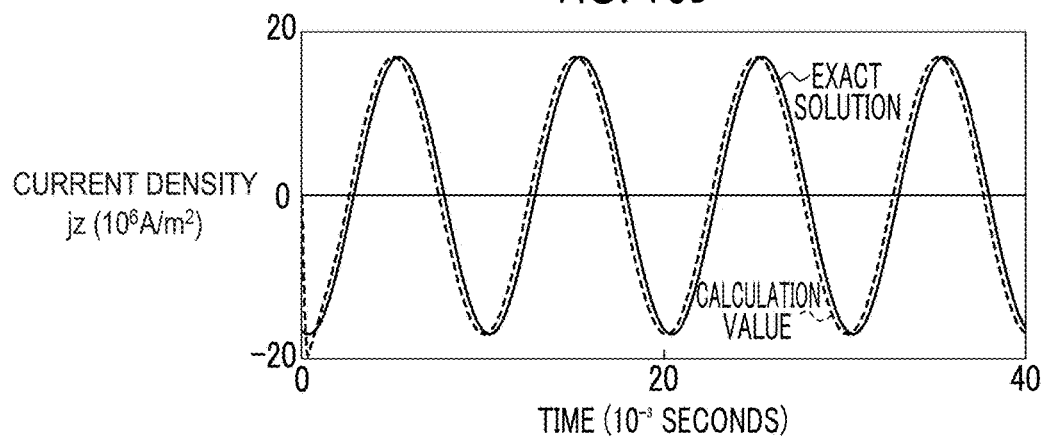
Figure 13C:
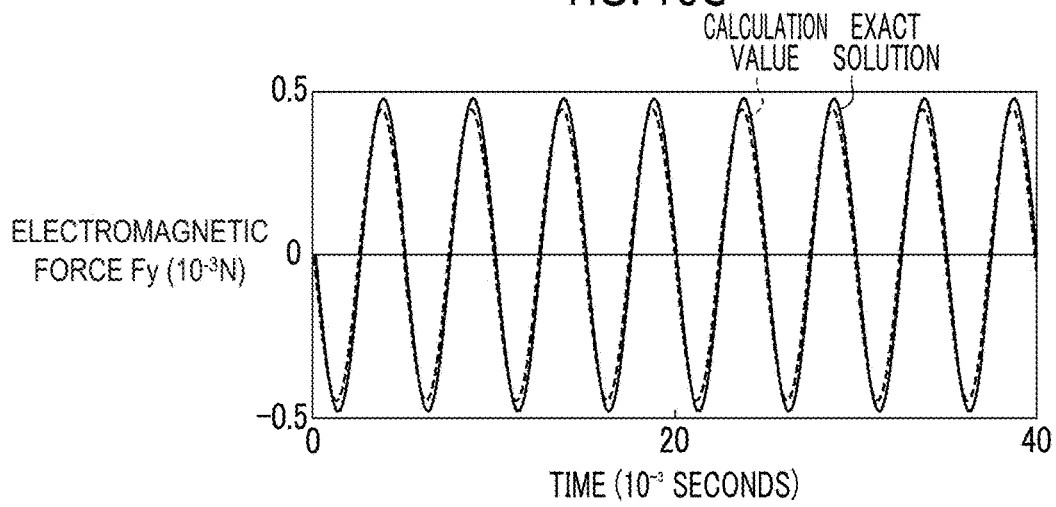

FIGS. 13A to 13C are graphs showing calculation values of a magnetic field on a conductive sphere surface, current density, and an electromagnetic force. FIGS. 13A to 13C respectively show time variations in the magnetic field Hx, current density jz, and electromagnetic force Fy at the gravity center position of a particle near a conductor surface. In the drawings, a value of an exact solution is indicated by a solid line, and a calculation value is indicated by a broken line. As shown in the drawings, it has been understood that, if the analysis method of this embodiment is used, a calculation result and an exact solution closely match each other.

As described above, the configuration and operation of the analyzer 100 according to the embodiments have been described. These embodiments are illustrative, and it will be understood by those skilled in the art that various modification examples may be made to the combination of the constituent elements or the processes and the modification examples still fall within the scope of the invention.

In the embodiments, although a case where the numerical calculation unit 120 calculates both the position and speed of the particle has been described, the invention is not limited thereto. For example, as a method of numerical analysis, like a Verlet method, there is a method which, when calculating the position of the particle, the position of the particle is calculated directly from a force applied to the particle without explicitly calculating the speed of the particle, and the technical spirit of this embodiment may be applied to the method.

It should be understood that the invention is not limited to the above-described embodiment, but may be modified into various forms on the basis of the spirit of the invention. Additionally, the modifications are included in the scope of the invention.

What is claimed is:

1. An analyzer comprising:
   a processor; and
   a memory coupled to the processor, the memory including a plurality of program modules executable by the processor, the plurality of program modules including:
   a magnetic moment application module configured to cause the processor to apply a magnetic moment to a particle system defined in a virtual space,
   a magnetic field calculation module configured to cause the processor to calculate a magnetic physical quantity related to the particle system including particles, to which the magnetic moment is applied by the processor as a result of executing the magnetic moment application module, and
   a particle state calculation module configured to cause the processor to numerically calculate a governing equation, which governs a movement of each particle, using the calculation result in the magnetic field calculation module,
   wherein the magnetic field calculation module causes the processor to numerically calculate an induction magnetic field in a particle group using an expression for an induction magnetic field derived by gauge transformation using a local gravity center vector representing a gravity center position of the particle group to be analyzed, in which particles within the particle group are not electrically insulated from one another,
   wherein the expression for the induction magnetic field is:

$$H(r_i) = -\frac{a^3}{6}\sum_{j\subset i}^{N_i}\sigma_j\left[\frac{\dot{B}_j - (n_{ij}\cdot\dot{B}_j)n_{ij}}{r_{ij}} - \frac{(r_{ij}\cdot d_{ii})\dot{B}_j - (r_{ij}\cdot\dot{B}_j)d_{ii}}{r_{ij}^3}\right] - $$

$$\frac{1}{6}\sigma_i a^2\dot{B}_i - \frac{1}{30}\sum_{j\subset i}^{N_i}\sigma_j a^5\frac{3(n_{ij}\cdot\dot{B}_j)n_{ij} - \dot{B}_j}{r_{ij}^3}$$

wherein a is a particle size, N is a number of particles, σ is an electrical conductivity, n is an expansion order of spherical harmonics, r is vector based on a radial position, B is a magnetic flux density, d is a vector based on the local gravity center vector, and i and j are integer indices.

2. The analyzer according to claim 1, wherein the magnetic field calculation module causes the processor to numerically calculate an induction magnetic field in the particle group using the expression for an induction magnetic field derived by transforming a vector potential of the particle system to a gauge described using a vector product of the local gravity center vector and the magnetic flux density of the particle system.

3. The analyzer according to claim 1, wherein a plurality of particle groups including a first particle group and a second particle group electrically insulated from each other are arrangeable in the particle system, and the magnetic field calculation module causes the processor to calculate an induction magnetic field in the first particle group using an expression for a first induction magnetic field derived by the gauge transformation using a first local gravity center vector representing the gravity center position of the first particle group and to calculate an induction magnetic field in the second particle group using an expression for a second induction magnetic field derived by the gauge transformation using a second local gravity center vector representing the gravity center position of the second particle group.

4. A non-transitory computer-readable medium storing thereon a computer program which, when executed by a processor of a computer, causes the computer to perform operations comprising:
   applying a magnetic moment to each of particles of a particle system defined in a virtual space;
   calculating a magnetic physical quantity related to the particle system including the particles, to which the magnetic moment is applied; and
   numerically calculating a governing equation, which governs a movement of each particle, using the calculation result of the magnetic physical quantity,
   wherein the calculating the magnetic physical quantity includes numerically calculating an induction magnetic field in a particle group using an expression for an induction magnetic field derived by gauge transformation using a local gravity center vector representing a gravity center position of the particle group to be analyzed, in which particles within the particle group are not electrically insulated from one another,
   wherein the expression for the induction magnetic field is:

$$H(r_i) = -\frac{a^3}{6}\sum_{j\subset i}^{N_i}\sigma_j\left[\frac{\dot{B}_j - (n_{ij}\cdot\dot{B}_j)n_{ij}}{r_{ij}} - \frac{(r_{ij}\cdot d_{ii})\dot{B}_j - (r_{ij}\cdot\dot{B}_j)d_{ii}}{r_{ij}^3}\right] - $$

-continued $$\frac{1}{6}\sigma_i a^2 \dot{B}_i - \frac{1}{30}\sum_{j\subset i}^{N_i} \sigma_j a^5 \frac{3(n_{ij}\cdot \dot{B}_j)n_{ij}-\dot{B}_j}{r_{ij}^3}$$

wherein a is a particle size, N is a number of particles, σ is an electrical conductivity, n is an expansion order of spherical harmonics, r is vector based on a radial position, B is a magnetic flux density, d is a vector based on the local gravity center vector, and i and j are integer indices.

5. An analyzer comprising:

a magnetic moment application hardware component configured to apply a magnetic moment to a particle system defined in a virtual space;

a magnetic field calculation hardware component configured to calculate a magnetic physical quantity related to the particle system including particles, to which the magnetic moment is applied by the magnetic moment application hardware component; and a particle state calculation hardware component configured to numerically calculate a governing equation, which governs a movement of each particle, using the calculation result in the magnetic field calculation hardware component;

wherein the magnetic field calculation hardware component numerically calculates an induction magnetic field in a particle group using an expression for an induction magnetic field derived by gauge transformation using a local gravity center vector representing a gravity center position of the particle group to be analyzed, in which particles within the particle group are not electrically insulated from one another, wherein the expression for the induction magnetic field is:

$$H(r_i) = -\frac{a^3}{6}\sum_{j\subset i}^{N_i} \sigma_j \left[ \frac{\dot{B}_j - (n_{ij}\cdot \dot{B}_j)n_{ij}}{r_{ij}} - \frac{(r_{ij}\cdot d_{ii})\dot{B}_j - (r_{ij}\cdot \dot{B}_j)d_{ii}}{r_{ij}^3} \right] -$$

-continued $$\frac{1}{6}\sigma_i a^2 \dot{B}_i - \frac{1}{30}\sum_{j\subset i}^{N_i} \sigma_j a^5 \frac{3(n_{ij}\cdot \dot{B}_j)n_{ij}-\dot{B}_j}{r_{ij}^3}$$

wherein a is a particle size, N is a number of particles, σ is an electrical conductivity, n is an expansion order of spherical harmonics, r is vector based on a radial position, B is a magnetic flux density, d is a vector based on the local gravity center vector, and i and j are integer indices.

6. The analyzer according to claim 5, wherein the magnetic field calculation hardware component numerically calculates an induction magnetic field in the particle group using the expression for an induction magnetic field derived by transforming a vector potential of the particle system to a gauge described using a vector product of the local gravity center vector and the magnetic flux density of the particle system.

7. The analyzer according to claim 5, wherein a plurality of particle groups including a first particle group and a second particle group electrically insulated from each other are arrangeable in the particle system, and the magnetic field calculation hardware component calculates an induction magnetic field in the first particle group using an expression for a first induction magnetic field derived by the gauge transformation using a first local gravity center vector representing the gravity center position of the first particle group and calculates an induction magnetic field in the second particle group using an expression for a second induction magnetic field derived by the gauge transformation using a second local gravity center vector representing the gravity center position of the second particle group.

* * * * *